US009340832B2

(12) United States Patent
Fu

(10) Patent No.: US 9,340,832 B2
(45) Date of Patent: *May 17, 2016

(54) METHODS FOR ENRICHING A VARIANT NUCLEIC ACID FROM A NUCLEIC ACID POPULATION IN A SAMPLE

(75) Inventor: Guoliang Fu, Oxford (GB)

(73) Assignee: 360 Genomics Limited (GB)

( * ) Notice: Subject to any disclaimer, the term of this patent is extended or adjusted under 35 U.S.C. 154(b) by 1050 days.

This patent is subject to a terminal disclaimer.

(21) Appl. No.: 12/529,204

(22) PCT Filed: Feb. 29, 2008

(86) PCT No.: PCT/GB2008/000707
§ 371 (c)(1),
(2), (4) Date: Mar. 22, 2010

(87) PCT Pub. No.: WO2008/104794
PCT Pub. Date: Sep. 4, 2008

(65) Prior Publication Data
US 2010/0227320 A1   Sep. 9, 2010

(30) Foreign Application Priority Data

Mar. 1, 2007   (GB) .................................. 0703996.9

(51) Int. Cl.
*C12Q 1/68*   (2006.01)

(52) U.S. Cl.
CPC .................................. *C12Q 1/6858* (2013.01)

(58) Field of Classification Search
None
See application file for complete search history.

(56) References Cited

U.S. PATENT DOCUMENTS

| | | | |
|---|---|---|---|
| 5,487,972 | A | 1/1996 | Gelfand et al. |
| 5,723,591 | A | 3/1998 | Livak et al. |
| 5,849,497 | A | 12/1998 | Steinman |
| 5,891,625 | A | 4/1999 | Buchardt et al. |
| 5,972,610 | A | 10/1999 | Buchardt et al. |
| 6,174,670 | B1 | 1/2001 | Wittwer et al. |
| 6,258,569 | B1 | 7/2001 | Livak et al. |
| 6,458,544 | B1 | 10/2002 | Miller |
| 6,808,897 | B2 * | 10/2004 | Shaw et al. ............. 435/69.1 |
| 7,141,377 | B2 | 11/2006 | Gelfand et al. |
| 8,440,405 | B2 * | 5/2013 | Fu .......................... 435/6.12 |
| 2001/0016323 | A1 | 8/2001 | Parkhurst et al. |
| 2002/0098510 | A1 | 7/2002 | Su et al. |
| 2002/0115080 | A1 | 8/2002 | Skouv et al. |
| 2003/0186314 | A1 | 10/2003 | Kambara et al. |
| 2004/0101893 | A1 * | 5/2004 | Kutyavin et al. ............. 435/6 |
| 2004/0248095 | A1 | 12/2004 | Behlke et al. |
| 2006/0183136 | A1 | 8/2006 | Pont-Kingdon et al. |
| 2007/0207494 | A1 | 9/2007 | Guo |

FOREIGN PATENT DOCUMENTS

| | | |
|---|---|---|
| EP | 2000/1061135 | 12/2000 |
| FR | 2779154 | 12/1999 |
| WO | 91/02087 | 2/1991 |
| WO | WO9325706 | 12/1993 |
| WO | WO9818965 | 5/1998 |
| WO | 99/61661 | 12/1999 |
| WO | WO9961561 | 12/1999 |
| WO | WO 0047766 A1 * | 8/2000 |
| WO | 03/027309 | 4/2003 |
| WO | WO03095680 | 11/2003 |
| WO | 2004/048612 | 6/2004 |
| WO | 2004/065628 | 8/2004 |
| WO | 2004/074447 | 9/2004 |
| WO | WO2007008997 | 1/2007 |
| WO | WO2007045890 | 4/2007 |
| WO | WO2007106534 | 9/2007 |

OTHER PUBLICATIONS

Neoh et al. Journal of Clinical Pathology (1999) 52: 766-769.*
Garcia de Viedma et al. Journal of Clinical Microbiology (2002) 40(3): 988-995.*
Liu et al. Nucleic Acids Research (2002) 30(2): 598-604.*
Whitcombe et al. Nature Biotechnology (1999) 17: 804-807.*
Latorra et al. Human Mutation (2003) 22(1): 79-85.*
Harris et al. BioTechniques 54: 93-97 (2013).*
EPO Examination Report dated Aug. 16, 2010 (7 pages).
Seyama, et al., Nucleic Acid Res. 1992, 20: 2493-6: A novel blocker-PCR method for detection of rare mutant alleles in the presence of an excess amount of normal DNA. Uses WT-specific blockers flanked by two amplification primers.
Parsons et al., Methods Mol Biol. 2005: 291: 235-45: Allele-specific competitive blocker-PCR detection of rare base substitution. Hybridization of WR-specific blocking primer blocks amplification of WT sequence; mutant templates are preferentially amplified by allele-specific PCR.
Orum, et al., Nucleic Acid Res. 1993, 21: 5332-6; Single base pair mutation analysis by PNA directed PCR clamping. PNAs bind, but they do not prime for extension. Allows selective amplification of target sequences that differ by one base pair.
McKinzie, et al., Mutat Res. 517: 209-20; Detection of rare K-ras condon 12 mutations using allele-specific competitive blocker PCR.
Jeffreys, et al., Genome Res. 2003, 13: 2316-2324; DNA enrichment by allele specific hybridization (DEASH): A novel method for haplotyping and for detecting low-frequency base substitutional variants and recombinant DNA molecules.

(Continued)

*Primary Examiner* — Angela M Bertagna
(74) *Attorney, Agent, or Firm* — Andrus Intellectual Property Law, LLP

(57) ABSTRACT

This invention provides methods and kits for enriching and/or detecting a nucleic acid with at least one variant nucleotide from a nucleic acid population in a sample. Methods employ the use of enriching primers and bridge-probes for enriching and detecting target nucleic acids. Extension of the enriching primer permits amplification of the target nucleic acid having the variant nucleotide.

21 Claims, 13 Drawing Sheets

(56) References Cited

OTHER PUBLICATIONS

Holland, P.M. et al., "Detection of specific polymerase chain reaction product by utilizing the 5'-3' exonuclease activity of thermus aquaticus DNA polymerase," Proc. Natl. Acad. Sci. USA (1991) 88:7276-7280.

Salmon, P.M., "Technoscope: La PCR en temps reel," Biofutur (2002) 219:2-8.

International Search Report and Written Opinion for Application No. PCT/GB08/00699 dated Jul. 30, 2008 (13 pages).

International Search Report and Written Opinion for Application No. PCT/GB08/00707 dated Sep. 26, 2008 (18 pages).

* cited by examiner

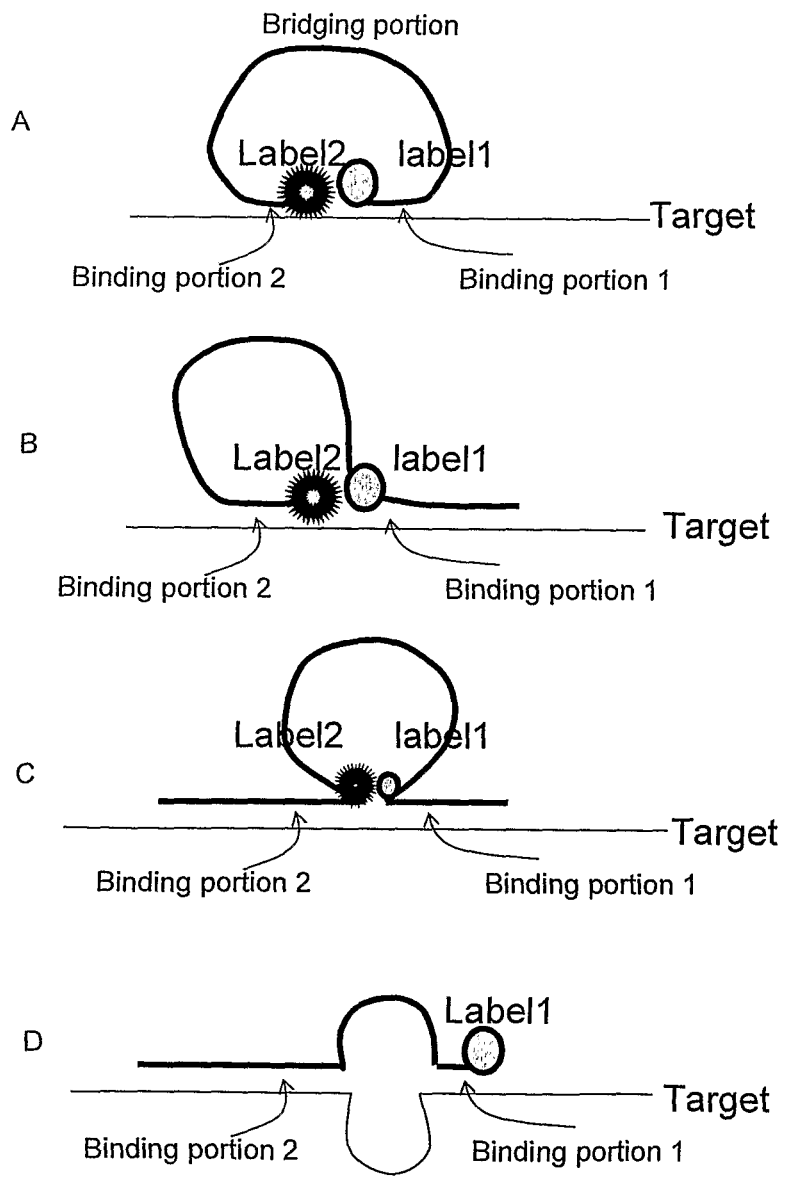

E

F

G

H

I

Scan unknown mutations

A

B

A

Using Bridge-probe for detection SNP or mutation

B

METHODS FOR ENRICHING A VARIANT NUCLEIC ACID FROM A NUCLEIC ACID POPULATION IN A SAMPLE

CROSS-REFERENCE TO RELATED APPLICATIONS

This patent application is a national stage filing under 35 U.S.C. 371 of International Application No. PCT/GB2008/000707, filed on Feb. 29, 2008, which claims foreign priority benefits to United Kingdom Patent Application No. 0703996.9, filed on Mar. 1, 2007. These applications are incorporated herein by reference in their entireties.

BACKGROUND OF THE INVENTION

The present invention relates to the field of detection and enrichment of a desired nucleic acid from a population of nucleic acids in a sample, especially the enrichment of rare nucleic acids containing mutations.

Single nucleotide polymorphisms (SNPs) are the most common type of variation in the human genome. Point mutations are also usually SNPs but the term mutation is normally reserved for those SNPs with a frequency rarer than 1% and/or where there is a known correlative or functional association between the mutation and a disease (Gibson N J, 2006 Clin Chim Acta. 363(1-2):32-47). There are many applications for genotyping polymorphisms and detecting rare mutations. Rare variant detection is important for the early detection of pathological mutations, particularly in cancer. For instance, detection of cancer-associated point mutations in clinical samples can improve the identification minimal residual disease during chemotherapy and detect the appearance of tumour cells in relapsing patients. The detection of rare point mutations is also important for the assessment of exposure to environmental mutagens, to monitor endogenous DNA repair, and to study the accumulation of somatic mutations in aging individuals. Additionally, more sensitive methods to detect rare variants can revolutionise prenatal diagnosis, enabling the characterisation of foetal cells present in maternal blood. A vast number of methods have been introduced, but no single method has been widely accepted. Many methods for detecting low-frequency variants in genomic DNA use the polymerase chain reaction (PCR) to amplify mutant and wild-type targets. The PCR products are analysed in a variety of ways, including sequencing, oligonucleotide ligation, restriction digestion, mass spectrometry or allele-specific hybridization to identify the variant product against a background of wild-type DNA. Other methods use allele-specific PCR to selectively amplify from the low-frequency variant, with or without additional selection. For example, by digesting PCR products with a restriction enzyme that specifically cleaves the wild-type product. Current approaches have inherent limitations due to the lack of total specificity of allele-specific primers during PCR, which creates false positives. As a result, all current approaches have limited sensitivity and accuracy (review in Jeffreys A J and May C A, 2003 Genome Res. 13(10):2316-24).

Most mutation detection systems yield an assay signal that is difficult to validate in terms of the number of mutant molecules detected. This can be overcome in part by analyzing multiple samples, each containing limited DNA (typically 50 genome equivalents), to determine the number of mutant molecules in the sample. (digital PCR; Vogelstein and Kinzler 1999 Proc Natl Acad Sci USA. 96(16):9236-41). However, the large number of PCR reactions required, combined with background noise arising from misincorporation of nucleotides during PCR is likely to limit this approach to detection levels of about 1 variant in a population of 1000 nucleic acids. Another limitation of many mutation detection procedures is that they replace the mutant site with a PCR primer sequence and yield short amplicons containing little, if any, information other than the presence of a putative mutant allele (review in Jeffreys A J and May C A, 2003).

The unifying problem behind all of these PCR approaches for detecting rare variants is replication infidelity during amplification. Jeffreys and May have provided a solution by enriching mutant DNA molecules from genomic DNA prior to analyzing them by PCR; a process called DNA enrichment by allele-specific hybridization (DEASH) (Genome research 13:2316-2324, 2003). This method is a modification of traditional nucleic acid-enriching techniques that utilise hybridization with biotinylated DNA probes. It uses allele-specific oligonucleotides to fractionate DNA molecules differing by a single base substitution. However, this method of DNA enrichment involves multiple steps, requires large amounts of starting material and suffers from low sensitivity and efficiency.

Another enriching method is based on Restriction Fragment Length Polymorphism (RFLP), where PCR-amplified products are digested with restriction enzymes that can selectively digest either a normal or a mutated allele. Enriched PCR is a modification introduced into the RFLP analysis. The principle of this approach is to create a restriction enzyme site only within normal sequences, thus enabling selective digestion of the normal alleles amplified in a first amplification step. This prevents the non-mutant DNA from further amplification in a second amplification step while, upon subsequent amplification, the mutated alleles are enriched (U.S. Pat. No. 5,741,678; Kahn et al, 1991). This approach is limited, however, to the analysis of mutations at precise locations where restriction enzyme sites naturally occur. To overcome this limitation, one can artificially introduce restriction enzyme sites near the site of the point mutation to distinguish between normal and mutant alleles. In this approach, base-pair substitutions are introduced into the primers used for the PCR, yielding a restriction enzyme site only when the primer flanks a specific point mutation. This approach enables the selective identification of a point mutation at a known site, presumably in any gene.

Mismatched 3' end amplification is a PCR technique which utilizes primers that have been modified at the 3' end to match only one specific point mutation. This method relies on conditions which permit extension from primers with 3' ends complementary to specific mismatches, whereas wild-type sequences are not extended. This procedure requires specific primers for each mutation and the PCR conditions are quite rigorous.

Recently, enrichment methods called PNA (or LNA) clamp PCR have been developed. High affinity nucleic acid analogues such as peptide-nucleic acids (PNAs) are used to inhibit nucleic acid amplification (U.S. Pat. No. 5,891,625). These methods can be problematic, however. It is difficult to find the optimal conditions for the PNA/LNA clamp; lengthy testing and redesigning are often required, and the purchase of specialised instruments may be needed. Furthermore, PNAs are expensive and difficult to synthesise and the efficiency of inhibition is often low.

EP1061135 relates to methods for detecting and identifying sequence variations in a nucleic acid sequence of interest using a detector primer. The publication concerns utilises diagnostics mismatches between the detector primer and the target where it occurs. The detector primer hybridizes to the sequence of interest and is extended with polymerase. The efficiency of detector primer extension is generally directly detected as an indication of the presence and/or identity of the sequence variation in the target Nevertheless, it will therefore be appreciated that the provision of novel methods and probes adapted for sensitive enrichment and detection of rare point mutations would be a contribution to the art.

SUMMARY OF THE INVENTION

The methods of the present invention allow for rapid, sensitive, and improved enrichment and detection of desired nucleic acids from a nucleic acid population. The improved methodology and probe also allow for rapid and sensitive detection of genetic variations in nucleic acids in samples from patients with genetic diseases or neoplasias.

Various aspects of the invention are described in the aspects, embodiments and claims below.

Generally speaking, in one aspect, the invention provides a method for enriching and/or detecting a desired nucleic acid with a particular target sequence (e.g. at least one variant nucleotide) from a nucleic acid population in a sample, said method comprising:
(a) treating the nucleic acid population under hybridisation conditions with a first enriching primer and a first amplification primer for a first strand of a target nucleic acid sequence such that said primers anneal to the first strand of the target nucleic acid such that the 3' end of the amplification primer is adjacent to or upstream of the 5' end of the enriching primer;
    wherein the nucleotide sequence of said enriching primer is such that it is substantially complementary to a diagnostic region of the first strand (for example where the suspected variant nucleotide is located and the 3' terminal nucleotide of the enriching primer is either complementary to the suspected variant nucleotide, or to the corresponding normal—non-variant—nucleotide),
(b) maintaining the mixture of step (a) under extension conditions (e.g. which may comprise appropriate nucleoside triphosphates and a nucleic acid polymerase, and the presence of appropriate reverse primers in step (a)),
    whereby extension of the annealed enriching primer is dependent on the presence of the normal or variant nucleotide in the target nucleic acid, and whereby synthesis of the enriching primer extension product either blocks extension of the amplification primer (which is hybridised to the target nucleic acid which includes the normal nucleotide) or promotes hybridisation and extension of the amplification primer (to the target nucleic acid which includes the variant nucleotide).

Thus, briefly, in one preferred embodiment of the present invention, extension of the amplification primer (and hence exponential amplification) depends on there being NO extension from the enriching primer. The unextended enriching primer will thus be dissociated from the target sequence under the extension conditions, thereby allowing extension of the amplification primer to pass through the diagnostic region containing suspected variant nucleotide and preferably for exponential amplification to occur.

In another embodiment, in step (a) the nucleic acid template forms a stem-loop structure under hybridisation conditions, wherein the double-stranded stem comprises an amplification primer binding site and the loop comprises the target nucleic acid sequence, wherein the enriching primer anneals to the diagnostic region in the loop. In step (b) the enriching primer is extended when it anneals to the diagnostic region containing a variant nucleotide; this extension opens up the stem loop structure thereby allowing the amplification primer to anneal to the primer binding site under hybridisation conditions and promoting amplification, wherein the enriching primer is not extendable when it anneals to the diagnostic region with a normal nucleotide, whereby the stem-loop structure is intact and prevents an amplification primer from annealing to the primer binding site.

Thus in both embodiments there are 2 different enriching primers, one of which is extended when it anneals to the diagnostic region containing a normal nucleotide, and one which is extended when it anneals to the diagnostic region containing a variant nucleotide.

In both embodiments, preferential amplification of the variant sequence is dependent on extension of one, but not the other, of the enriching primers.

However in the first embodiment it is extension of the 'normal' enriching primer which leads ultimately to the preferential amplification of the variant sequence (by blocking extension of the amplification primer annealed to the 'normal' target) as illustrated for example in FIG. 1.

In the second embodiment it is extension of the 'variant' enriching primer which leads ultimately to the preferential amplification of the variant sequence (by permitting only extension of the amplification primer annealed to the 'variant' target) as illustrated for example in FIG. 11.

Preferably the extension product of the enriching primer itself is rendered unsuitable for exponential amplification, e.g. by making the enriching primer unsuitable for copying either by the incorporation of an appropriate moiety, or due to its sequence (which may fold on itself to prevent primer annealing).

As described below, extension of the annealed enriching primer may be made dependent on the presence of the normal or variant nucleotide in the target nucleic acid in a number of ways.

For example the primer may at its 3' terminus include a nucleotide complementary to the normal or wild-type sequence. This is required for primer extension. It will be appreciated in this context that where any aspect or claim herein refers to "3' terminal nucleotide" or "3' terminus" the invention may be likewise practised with a non-terminal nucleotide which is in sufficient proximity to the terminal nucleotide to achieve the same effect i.e. to permit or prevent extension when the relevant primer is annealed to the diagnostic portion which is complementary or non-complementary respectively. Typically such non-terminal nucleotides would nevertheless be separated by only 1, 2, or 3 nucleotides from the terminus.

For example the primer may at its 3' terminus include a blocking nucleotide that is non-complementary to the normal or wild-type sequence. Conditions are applied which will remove this terminal nucleotide due to the mismatch (e.g. proof reading polymerase) and the blocking effect obviated, permitting extension.

For example the primer may at its 3' terminus include a blocking nucleotide that is complementary to the normal sequence Conditions are applied which will remove this terminal nucleotide (e.g. pyrophosphorylysis) and the blocking effect obviated, permitting extension.

In another aspect, the invention provides a method for detecting a target nucleic acid, wherein said detecting is mediated by a bridge-probe, which comprises at least two binding portions linked by a bridging portion, wherein the first binding portion is capable of hybridising to a first region of a nucleic acid template, wherein the second binding portion is capable of hybridising to a second region of the nucleic acid template adjacent or substantially adjacent to the first region of the template nucleic acid, wherein the first region of the template nucleic acid includes the suspected variant nucleotide.

The length and/or composition of said bridging portion combined with the degree of separation, if any, between the first region and second region of the template nucleic acid, is capable of regulating the Tm (melting temperature) of the individual binding portion and/or the Tm of the bridge-probe, and these variables can be readily selected or adapted in the light of the present disclosure by those skilled in the art e.g. using conventional software.

The first region of a nucleic acid template may be a region on the extended target sequence of a primer extension product, wherein said second region is a part of an amplification primer or a probe.

In use, one binding portion of the bridge-probe hybridises to the target nucleic acid at different melting temperatures dependent on whether the target includes complementary or non-complementary nucleotides. The temperatures are measured and are indicative of the presence or absence of a suspected variant nucleotide.

The bridging portion comprises at least one nucleotide or at least one non-nucleotide chemical moiety.

The bridge-probe and/or primer or probe may comprise detection labels. The first binding portion is attached to one or more first labels, the second binding portion is attached to one or more second labels, wherein said first labels and second labels are contact quenching pairs, wherein one of the labels is a quencher, wherein upon hybridization of the probes with the target sequence the first and second labels are in a contact quenching relationship. Alternatively, the first binding portion is attached to a first label, and the second binding portion is attached to a second label, wherein said first label and second label are fluorescence energy transfer pairs, wherein upon hybridization of the probes with the target sequence the first and second labels are in a fluorescence resonance energy transfer (FRET) relationship. The second binding portion and the region of the primer which is capable of hybridising with the second binding portion of the bridge probe may be each be attached to one member of a fluorophore and a quencher pair such that upon hybridization of the bridge-probe with the target sequence the fluorophore and quencher are in a contact quenching relationship. It is preferred that a quencher is a non-fluorescent entity. The quencher may be a nanoparticle. The quencher may be G residue or multiple G residues.

The present invention also provides a method for analyzing a target DNA sequence of a biological sample, said method comprising the steps of
(a) adding to the biological sample an effective amount of amplification primers and a nucleic acid probe,
  wherein one of said amplification primers and the probe are each labelled with one member of a fluorophore and a quencher such that upon hybridization of the probes with amplified product comprising the labelled amplification primer, the fluorophore and quencher are in a contact quenching relationship,
(b) amplifying the target nucleic acid sequence by an amplification method;
(c) illuminating the biological sample with light of a selected wavelength that is absorbed by said fluorophore; and
(d) detecting the fluorescence emission of the said fluorophore or monitoring the temperature-dependent fluorescence from said fluorophore.

Generally speaking the labelled probe will hybridise to the amplified product in sufficient proximity to the primer to achieve this, and those skilled in the art will be able to target it accordingly depending on the labelled sites e.g. closely within the extended region near the primer and\or in part hybridising to the primer itself. Typically 5 or fewer (e.g. 0, 1, 2, 3, or 4) nucleotides would separate the near end of the probe and 'terminus' of the primer extended the amplification product.

In another embodiment, a method for analyzing a target DNA sequence of a biological sample comprises the steps of
(a) adding to the biological sample an effective amount of amplification primers and two nucleic acid probes that hybridize to adjacent regions of the target sequence,
  one of said probes being labelled with a fluorophore and the other probe labelled with a quencher of a contact quenching pair such that upon hybridization of the probes with the amplified product of the target sequence the fluorophore and quencher are in a contact quenching relationship, wherein the fluorophore and quencher are within 5 nucleotides of one another;
(b) amplifying the target nucleic acid sequence by an amplification method;
(c) illuminating the biological sample with light of a selected wavelength that is absorbed by said fluorophore; and
(d) detecting the fluorescence emission of the said fluorophore or monitoring the temperature-dependent fluorescence from said fluorophore.

The above methods may further comprise the step of determining a melting profile of the probe and target duplex. It is preferred that one of said nucleic acid probes is a bridge-probe, which comprises at least two binding portions linked by a bridging portion, wherein first binding portion is capable of hybridising to a first region of a template nucleic acid (here: the amplified product of the target sequence), wherein second binding portion is capable of hybridising to a second region of the template nucleic acid adjacent or substantially adjacent to the first region of the template nucleic acid, wherein said bridging portion comprises at least one nucleotide or at least one non-nucleotide chemical moiety that is incapable of hybridising to the nucleic acid template, wherein the length and/or composition of said bridging portion is one of the factors determining the Tm of the individual binding portion and/or the Tm of the bridge-probe, wherein the first region of the template nucleic acid includes the suspected variant nucleotide.

Also provided are related methods and materials (e.g. kits and probes).

All combinations of the various embodiments and claims (including dependent claims) described below apply mutatis mutandis to the aspects of the invention as described above.

The annealed enriching primer is extended on the template containing appropriate normal nucleotide under an extension condition which comprises at least one modified deoxynucleoside triphosphate. The enriching primer within the extended strand is degraded by a 5' exonuclease activity but the extended strand (including the modified deoxynucleoside triphosphates) is resistant to the cleavage, thereby blocking extension from an upstream amplification primer.

The annealed enriching primer is not extended on the template containing the variant nucleotide and is dissociated from the template, allowing the extension of an upstream amplification primer to pass through the diagnostic region.

The (partially degraded) enriching primer extension product can be partially copied in a linear manner, whereas the amplification primer extension product can be amplified exponentially.

Figure 5:
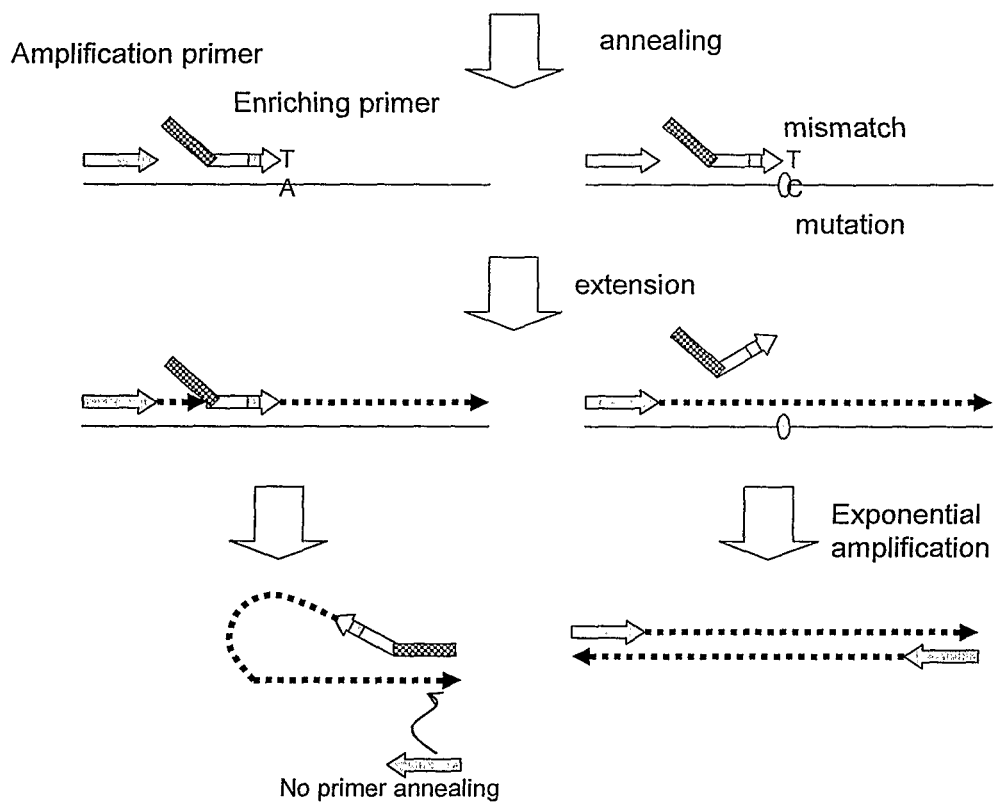

FIG. 5 is a schematic diagram of an embodiment of the present invention showing an enriching primer comprising a 5' tail sequence. The 5' tail sequence is identical or substantially identical to the sequence of the second amplification primer for the second strand of target sequence, which is complementary to the first strand of the target sequence, to which the enriching primer and the first amplification primer are capable of annealing. The enriching primer anneals to a diagnostic region, wherein the 3' terminus nucleotide (T, thymidine) of the enriching primer matches to the normal nucleotide (A, adenosine) and mismatches to the variant nucleotide (C, cytidine) of a diagnostic region of the target sequence. The annealed enriching primer is extended on the template containing the appropriate normal nucleotide; the extended strand blocks extension from an upstream amplification primer. The annealed enriching primer is not extended on the template containing the variant nucleotide and is dissociated from the template, allowing the extension of an upstream amplification primer to pass through the diagnostic region. The enriching primer extension product, upon being subjected to denaturing and hybridising conditions, folds back to form a stem-loop structure which blocks the binding site for the second amplification primer, whereas the amplification primer extension product can be amplified exponentially.

Figure 6:
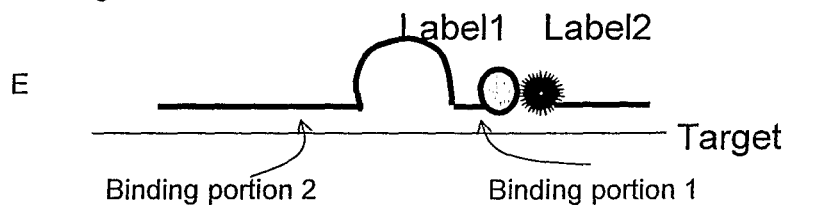
Figure 6:
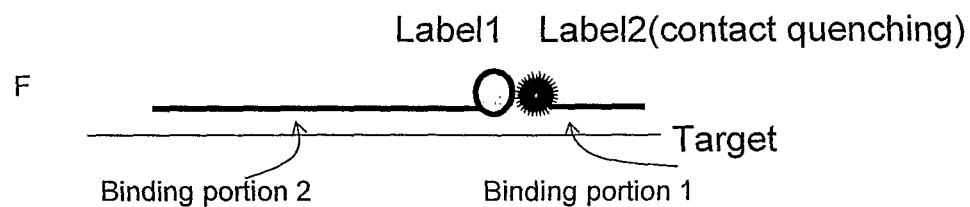
Figure 6:
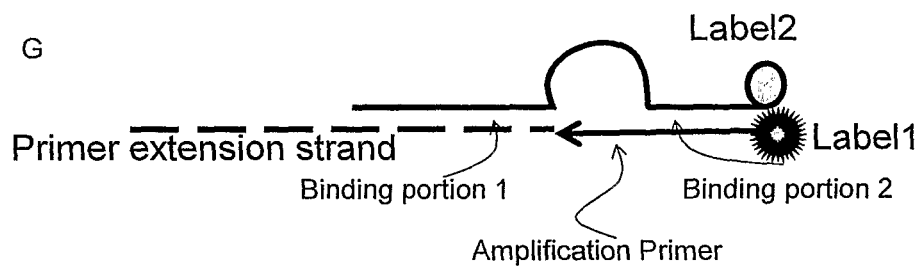
Figure 6:
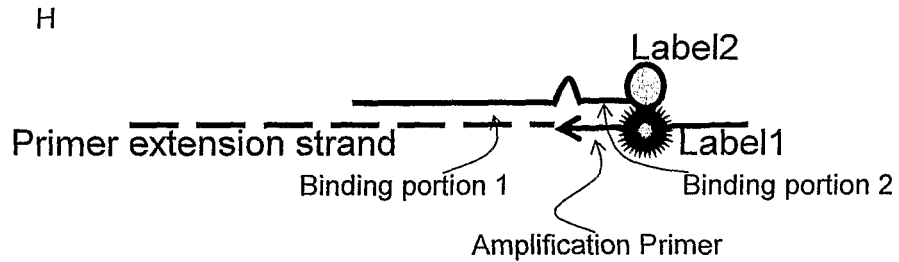
Figure 6:
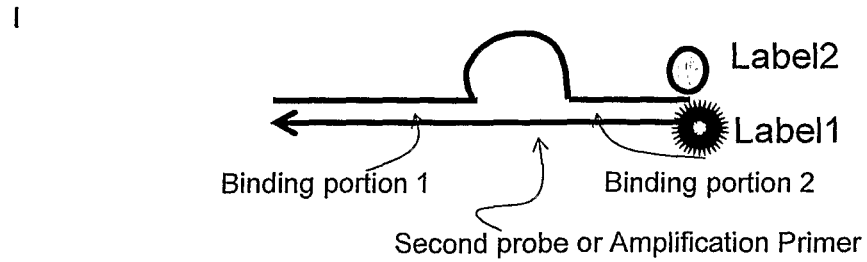
Figure 7:
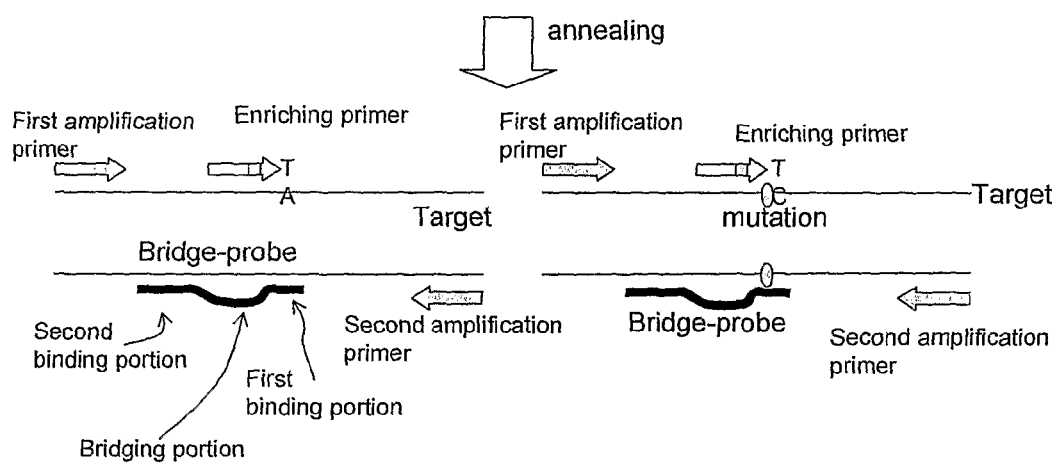

FIG. 6 illustrates various bridge-probes hybridised to target nucleic acids. (A) The ends of a bridge-probe point towards each other when the bridge-probe hybridises to a target nucleic acid. The ends of the bridge-probe are attached with different labels. When the bridge-probe is hybridised to the target, the two labels are brought into close proximity. (B) The ends of a bridge-probe point to the same direction when the bridge-probe hybridises to a target nucleic acid. The bridge-probe is attached with two labels. When the bridge-probe is hybridised to the target, the two labels are brought into close proximity. (C) The ends of a bridge-probe point away from each other when the bridge-probe hybridises to a target nucleic acid. The binding portions are labelled with different labels. The hybridisation brings the two labels into close proximity. (D) The two binding portions hybridise to the target, wherein the region of a target nucleic acid hybridised with the first binding portion is some distance away from the region hybridised with the second binding portion. (E) The bridge-probe is labelled with labell and another probe is labelled with label 2. When the two probes hybridise to the target, the two labels are in close proximity. (F) Two nucleic acid probes hybridise to adjacent regions of the target sequence, one of said probes being labelled with a fluorophore and the other probe labelled with a quencher of a contact quenching pair such that upon hybridization of the probes with the amplified products the fluorophore and quencher are in contact quenching relationship. (G), (H) and (I) Amplification primers and a nucleic acid probe which may be a bridge-probe are each labelled with one member of a fluorophore and a quencher such that upon hybridization of the probes with the amplified products the fluorophore and quencher are in a contact quenching relationship FIG. 7 illustrates a typical reaction of a method of the present invention for enrichment and detection of a point mutation in a sample. In the reaction, a first amplification primer and an enriching primer anneal to the first strand of target nucleic acid; a second amplification primer and a bridge-probe anneal to the second strand of target nucleic acid which is complementary to the first strand of target nucleic acid. The enriching primer anneals to a diagnostic region, wherein the 3' terminus nucleotide (T, thymidine) of the enriching primer matches to the normal nucleotide (A, adenosine), and mismatches to the variant nucleotide (C, cytidine) of a diagnostic region of the target sequence. The first binding portion of the bridge-probe anneals to the diagnostic region of the second strand of the target nucleic acid with a suspected variant nucleotide. The second binding portion of the bridge-probe anneals to a target region which is adjacent to the diagnostic region on the second target strand but is not overlapping or has limited overlap with the target region having the sequence substantially identical to the sequence of the enriching primer. In the other words, the bridge-probe and enriching primer have no or limited complementarity, thereby avoiding annealing with each other. The bridge-probe is labelled and generates a detectable signal when hybridising to a target nucleic acid or dissociating from a target nucleic acid. The bridge-probe can be used for real-time detection during amplification and enrichment, or can be used in a melting curve analysis for end point detection. The first binding portion of the bridge-probe hybridises to a perfectly matched target nucleic acid or a mismatched target nucleic acid at different melting temperatures, which are measured and are indicative of the presence or absence of a suspected variant nucleotide.

Figure 8:
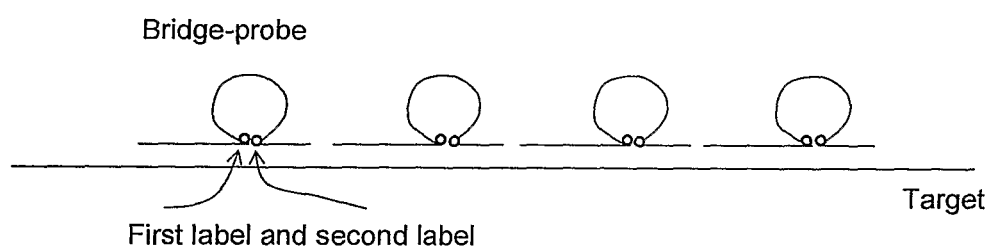

FIG. 8 illustrates a method using a set of bridge-probes to scan unknown mutations.

Figure 9:
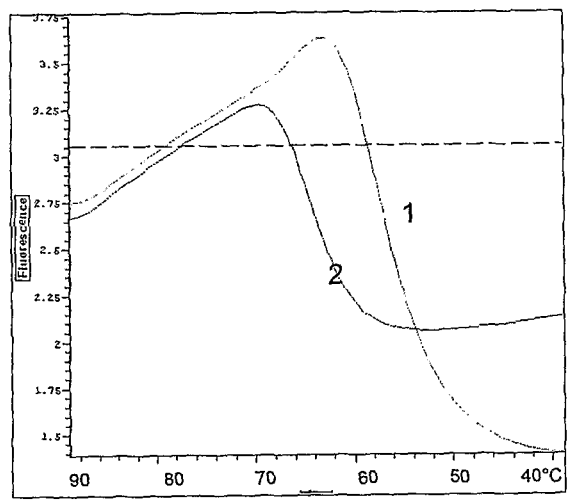
Figure 9:
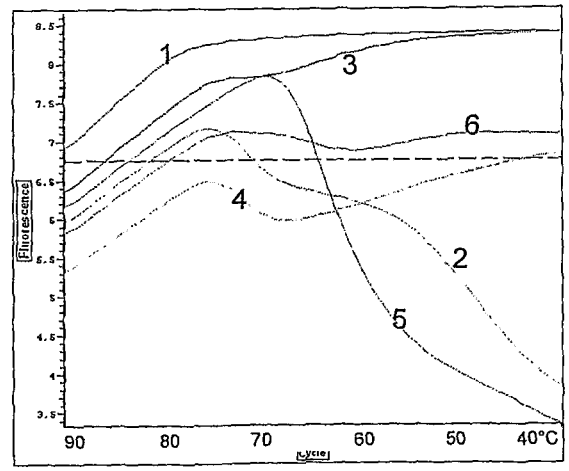

FIG. 9 shows results of melting curve analysis of bridge-probes from examples 2 (as shown in FIG. 9A) and 3 (as shown in FIG. 9B).

Figure 10:
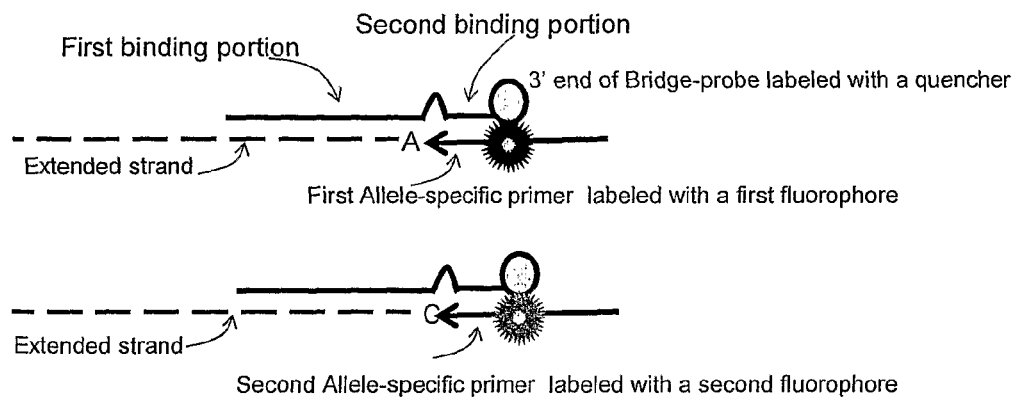
Figure 10:
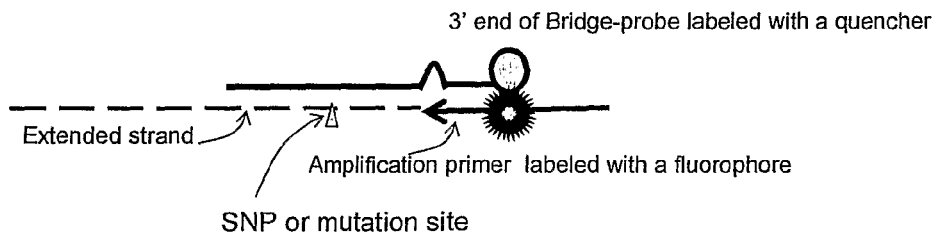

FIG. 10 shows using a bridge-probe for detection of a SNP or point mutation. In FIG. 10A, the first allele-specific primer is labelled with a first fluorophore, while the second allele-specific primer is labelled with second fluorophore. If the target SNP or mutation is present in a sample, one or both of the allele-specific primers are extended to produce the primer extension strand. A bridge-probe labelled with a quencher at the 3' end hybridises to the primer extension strand with the first binding, portion, while the second binding portion hybridises to the primer sequence. This hybridisation brings the fluorophore and quencher in a close contact quenching relationship. In FIG. 10B, one of the amplification primers capable of annealing to a region close to a SNP is labelled with a fluorophore. In the detection reaction, the labelled primer is extended to produce the primer extension strand. A bridge-probe labelled with a quencher at the 3' end hybridises to the primer extension strand with the first binding portion, while the second binding portion hybridises to the primer sequence. The first region that binds to the first binding portion of the bridge-probe contains the SNP or mutation site. This hybridisation makes the fluorophore and quencher in a close contact quenching relationship.

Figure 11:
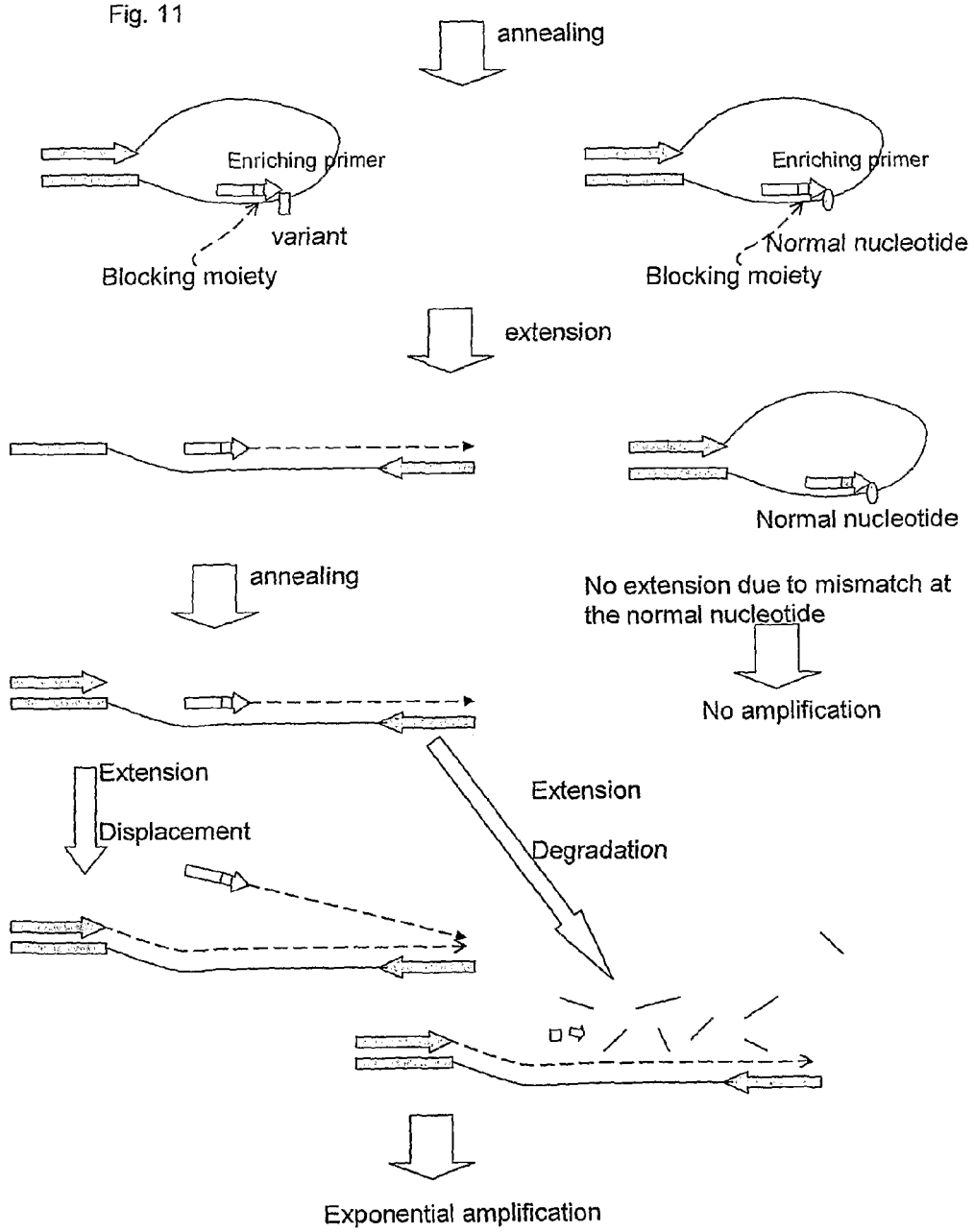

FIG. 11 illustrates a method of enriching and/or detecting a target nucleic acid using an enriching primer and amplification primers; the nucleic acid template is capable of forming a stem-loop structure.

Figure 12:
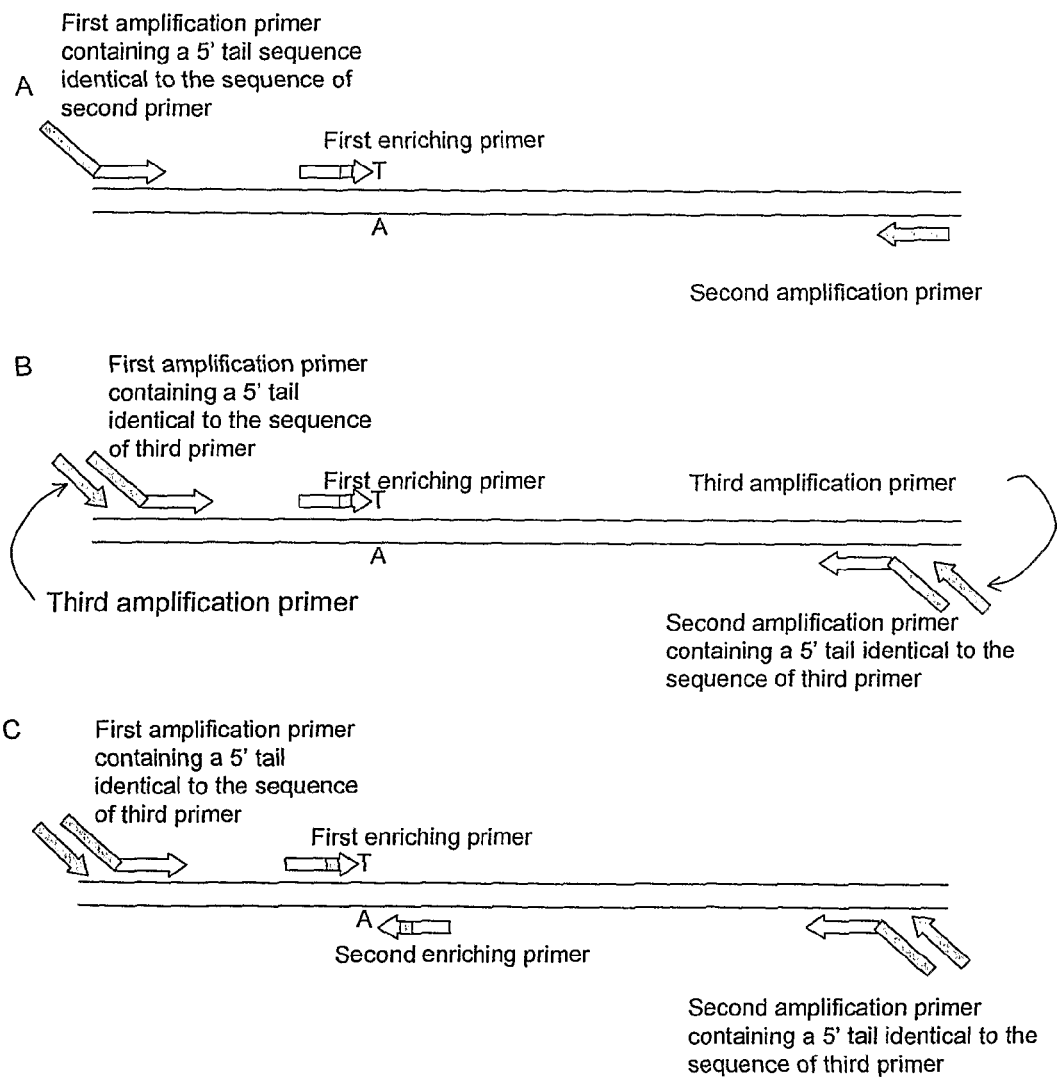

FIG. 12 shows amplification primers with 5' tail sequence. (A) nucleic acid template capable of forming a stem-loop structure is created by an extension of a first amplification primer with a 5' tail sequence. The 5' tail sequence comprises nucleotide or non-nucleotide sequence complementary to the binding site of the second amplification primer. In other words, the 5' tail sequence comprises nucleotide or non-nucleotide sequence identical or substantially identical to the sequence of the second primer. The first and second amplification primers are capable of hybridising to the extension product of the second and first amplification primers, respectively. (B) nucleic acid template capable of forming a stem-loop structure is created by an extension of first and second amplification primers with the same 5' tail sequence. The 5' tail sequence comprises nucleotide or non-nucleotide sequence complementary to the binding site of a third amplification primer. In other words, the 5' tail sequence comprises nucleotide or non-nucleotide sequence identical or substantially identical to the sequence of the third primer. The third primer may be an arbitrary universal primer unrelated to the target sequence. (C) shows a similar structure as (B) but with an additional second enriching primer annealed to the diagnostic region of the second strand of the target nucleic acid.

DETAILED DESCRIPTION OF THE INVENTION

The present invention is directed towards sensitive and improved methods and probes for detection and enrichment of desired nucleic acids from a mixed nucleic acid population for use in assays to detect and monitor gene expression or rare mutations in a test sample.

I. Materials

A. Target Nucleic Acid in a Sample

A sample refers to any substance containing or presumed to contain nucleic acid and includes a sample of tissue or fluid isolated from an individual or individuals. As used herein, the terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA. The oligonucleotide is comprised of a sequence of approximately at least 6 nucleotides, preferably at least 10-12 nucleotides, and more preferably at least 15-20 nucleotides corresponding to a region of the designated nucleotide sequence.

As used herein, the term "target sequence" or "target nucleic acid sequence" refers to a region which is to be either amplified, detected or both. The target sequence, which is the object of amplification and detection, can be any nucleic acid. The target sequence can be RNA, cDNA, genomic DNA or DNA from a disease-causing microorganism or virus. The target sequence can also be DNA treated by chemical reagents, various enzymes and physical exposure. A target nucleic acid sequence of interest in a sample may appear as single-stranded DNA or RNA such as cDNA, mRNA, other RNA or as separated complementary strands. Separating complementary strands of target nucleic acid may be accomplished by physical, chemical or enzymatic means.

B. Primers

The term "Primer" as used herein refers to an oligonucleotide, whether occurring naturally or produced synthetically, which is capable of acting as a point of initiation of synthesis when placed under conditions in which synthesis of a primer extension product complementary to a nucleic acid strand is induced i.e., in the presence of nucleotides and an agent for polymerization such as DNA polymerase and at a suitable temperature and buffering conditions. The primer is preferably single-stranded for maximum efficiency in amplification, but may alternatively be double-stranded. The primer must be sufficiently long to prime the synthesis of extension products in the presence of the inducing agent. The exact lengths of the primers will depend on many factors, including temperature, source of primer and use of the method.

The term "complementary to" is used herein in relation to nucleotides to mean a nucleotide that will base pair with another specific nucleotide. Thus adenosine triphosphate is complementary to uridine triphosphate or thymidine triphosphate and guanosine triphosphate is complementary to cytidine triphosphate. It is appreciated that whilst thymidine triphosphate and guanosine triphosphate may base pair under certain circumstances they are not regarded as complementary for the purposes of this specification. It will also be appreciated that whilst cytosine triphosphate and adenosine triphosphate may base pair under certain circumstances they are not regarded as complementary for the purposes of this specification. The same applies to cytosine triphosphate and uracil triphosphate.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, where the enriching primer comprises a nucleotide sequence in which the 3'-terminal nucleotide is complementary to either the suspected variant nucleotide or the corresponding normal nucleotide, a non-complementary nucleotide fragment may be attached to the 5'-end of the primer, with the remainder of the primer sequence being complementary to the diagnostic portion of the target base sequence. Commonly, however, the primers have exact complementarity except in so far as non-complementary nucleotides may be present at a predetermined primer terminus as hereinbefore described.

It will be appreciated, however, that in certain circumstances synthesis of a primer extension product might be induced to occur even in the presence of a non-complementary 3'-terminal residue. This artefactual result may arise from an annealing/incubation temperature that is too low (in which case the temperature may be increased), too long of an incubation/annealing time (in which case the time may be reduced), a salt concentration that is too high (in which case the salt concentration may be reduced), an enzyme or nucleoside triphosphate concentration that is too high, an incorrect pH, or an incorrect length of oligonucleotide primer. Artefactual results may be avoided by deliberately introducing one or more further mismatched residues, or if desired, deletions or insertions, within the diagnostic primer to destabilise the primer by further reducing the binding during hybridisation.

The term "enriching primer" as used herein to refer to the primer that has a nucleotide sequence such that it is substantially complementary to a diagnostic region where the suspected variant nucleotide is located. When an enriching primer anneals to a target sequence, it may be extended or may not be extended depending on the presence or absence of the suspected variant nucleotide. In one embodiment, when it anneals to the diagnostic region containing the suspected variant nucleotide, the annealed enriching primer may be non-extendable, whereby the enriching primer is dissociated from the target sequence under the extension condition, thereby allowing extension of the amplification primer to pass through the diagnostic region containing suspected variant nucleotide. When it anneals to the diagnostic region containing the corresponding normal nucleotide, the annealed enriching primer is extended to synthesize the enriching primer extension product whereby the extension from an upstream amplification primer is blocked by the enriching primer extension product. In another embodiment, the nucleic acid template forms a stem-loop structure under hybridisation conditions. The double-stranded stem portion comprises the amplification primer binding site; the loop comprises the target nucleic acid sequence. The enriching primer anneals to the diagnostic region in the loop. The enriching primer is extended when it anneals to the diagnostic region with a variant nucleotide, this extension opens up the stem-loop structure thereby allowing the amplification primer to anneal to the primer binding site and promoting amplification. The enriching primer may not be extendable when it anneals to the diagnostic region with a normal nucleotide, whereby the stem-loop structure is intact and is able to prevent an amplification primer from annealing to the primer binding site.

It is preferred that a terminal nucleotide of the enriching primer is selected to be either complementary to the suspected variant nucleotide or to the corresponding normal nucleotide such that an extension product of the enriching primer is synthesised when the enriching primer anneals to the diagnostic region containing a particular nucleotide, but no such extension product is synthesised when the enriching primer anneals to the diagnostic region containing no particular nucleotide of the target nucleic acid sequence.

The term "diagnostic region" as used herein means that region of the target nucleic acid sequence which contains the potential variant nucleotide as its terminal nucleotide or its internal nucleotide, the presence or absence of which is to be detected. It should be appreciated that the use of the terms "variant nucleotide", "normal nucleotide" or "mutant nucleotide" is situation dependent and may be interchangeable. In one situation, a nucleotide may be called variant or mutant, but in another situation, it may be called normal nucleotide.

The enriching primer may comprise a moiety that renders the extension product of the enriching primer unsuitable for an exponential amplification. In one embodiment, the moiety may be a blocking moiety (or referred to as a non-copiable moiety), wherein the replication of all or part of said enriching-primer is blocked, whereby the primer extension molecule generated from a template of the enriching primer extension strand is not suitable as a template for a further primer extension as it lacks a primer binding site. The blocking moiety may be hydrocarbon arm, an HEG, non-nucleotide linkage, abasic ribose, nucleotide derivatives or a dye. The blocking moiety may be located at less than 18 nucleotides away from 3' terminus of the enriching primer. It is preferred that the blocking moiety may be located at less than 6 nucleotides away from 3' terminus of the enriching-primer. It is more preferred that the blocking moiety may be located at less than 3 nucleotides away from 3' terminus of the enriching primer.

The primer for use in the disclosed methods in the present invention comprises a 3' sequence complementary to a target sequence, which is normally used for priming an extension reaction. This part of the primer is referred to as the 3' priming portion of the enriching primer. In another embodiment, the enriching primer may comprise additional sequences 5' of the priming portion of the enriching primer that may or may not be complementary to a target sequence; this additional sequence is referred to as a tail. In one embodiment, the enriching primer comprises a 5' tail sequence which is complementary or substantially complementary to a primer binding site on the enriching primer extension product. The enriching primer extension product, upon being subjected to denaturing and hybridising conditions, folds back to form a stem-loop structure which prevents a further primer binding.

Figure 1:
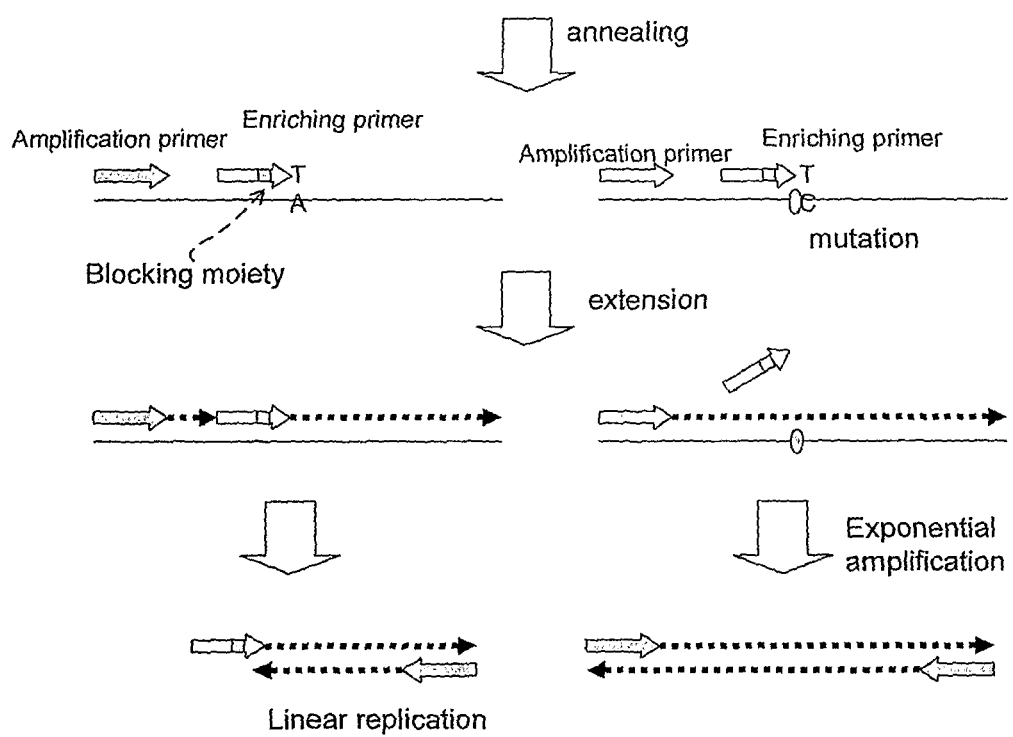
FIG. 1 is a schematic diagram of an embodiment of the present invention showing an enriching primer annealing to a diagnostic region, wherein the 3' terminus nucleotide (T, thymidine) of the enriching primer matches to the normal nucleotide (A, adenosine), and mismatches to the variant nucleotide (C, cytidine) of a diagnostic region of the target sequence. The annealed enriching primer is extended on the template containing the appropriate normal nucleotide, which blocks extension from an upstream amplification primer. The annealed enriching primer is not extended on the template containing the variant nucleotide and is dissociated from the template, allowing the extension of an upstream amplification primer to pass through the diagnostic region. The enriching primer extension product can be partially copied in a linear manner, whereas the amplification primer extension product can be amplified exponentially.
Figure 2:
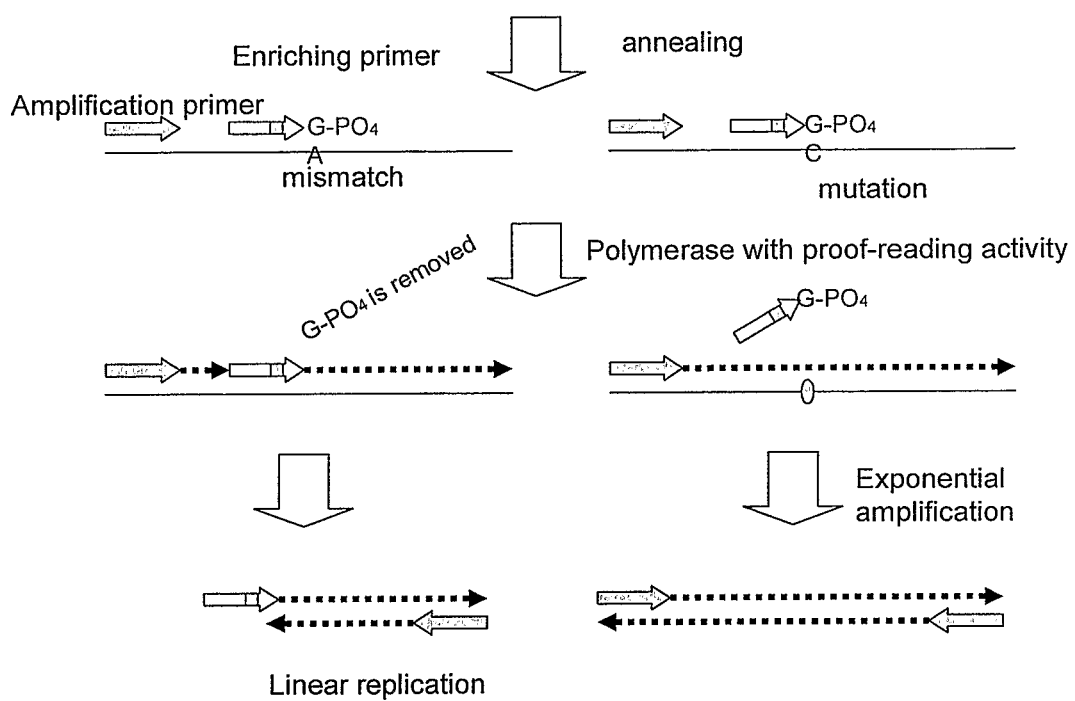
FIG. 2 is a schematic diagram of an embodiment of the present invention showing an enriching primer annealing to a diagnostic region, wherein the 3' terminus nucleotide (G, guanine) of the enriching primer, blocked by a phosphate group, matches to the variant nucleotide (C, cytidine), whereas it mismatches to the normal nucleotide (A, adenosine) of the diagnostic region. The annealed enriching primer is extended, with the terminal G removed by a proof-reading activity of a DNA polymerase, on the template containing appropriate normal nucleotide, which blocks extension from an upstream amplification primer. The annealed enriching primer is not extended on the template containing the variant nucleotide and is dissociated from the template, allowing the extension of an upstream amplification primer to pass through the diagnostic region. The enriching primer extension product can be partially copied in a linear manner, whereas the amplification primer extension product can be amplified exponentially.
Figure 3:
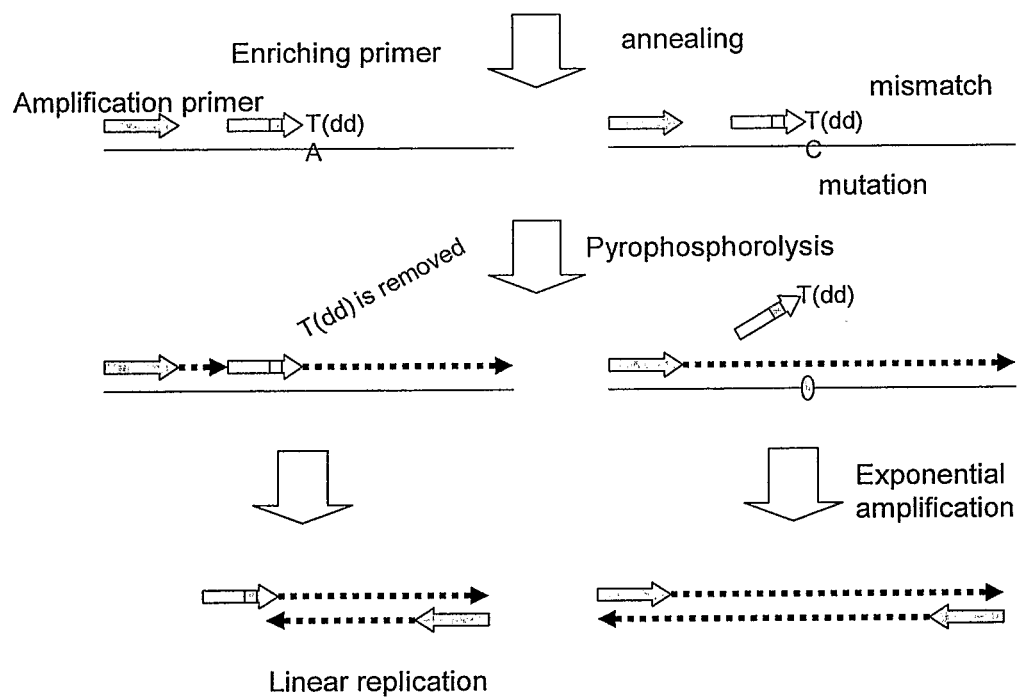
FIG. 3 is a schematic diagram of an embodiment of the present invention showing an enriching primer annealing to a diagnostic region, wherein the 3' terminus nucleotide (ddT, dideoxythymidine monophosphate) of the enriching primer matches to the normal nucleotide (A, adenosine), whereas it mismatches to the variant nucleotide (C, cytidine) of the diagnostic region. The annealed enriching primer is extended after the terminal T residue is removed by pyrophosphorolysis activity of a DNA polymerase on the template containing appropriate normal nucleotide, wherein the enriching primer extension product blocks extension of an upstream amplification primer. The annealed enriching primer is not extended on the template containing the variant nucleotide and is dissociated from the template, allowing the extension of an upstream amplification primer to pass through the diagnostic region. The enriching primer extension product can be partially copied in a linear manner, whereas the amplification primer extension product can be amplified exponentially.
Figure 4:
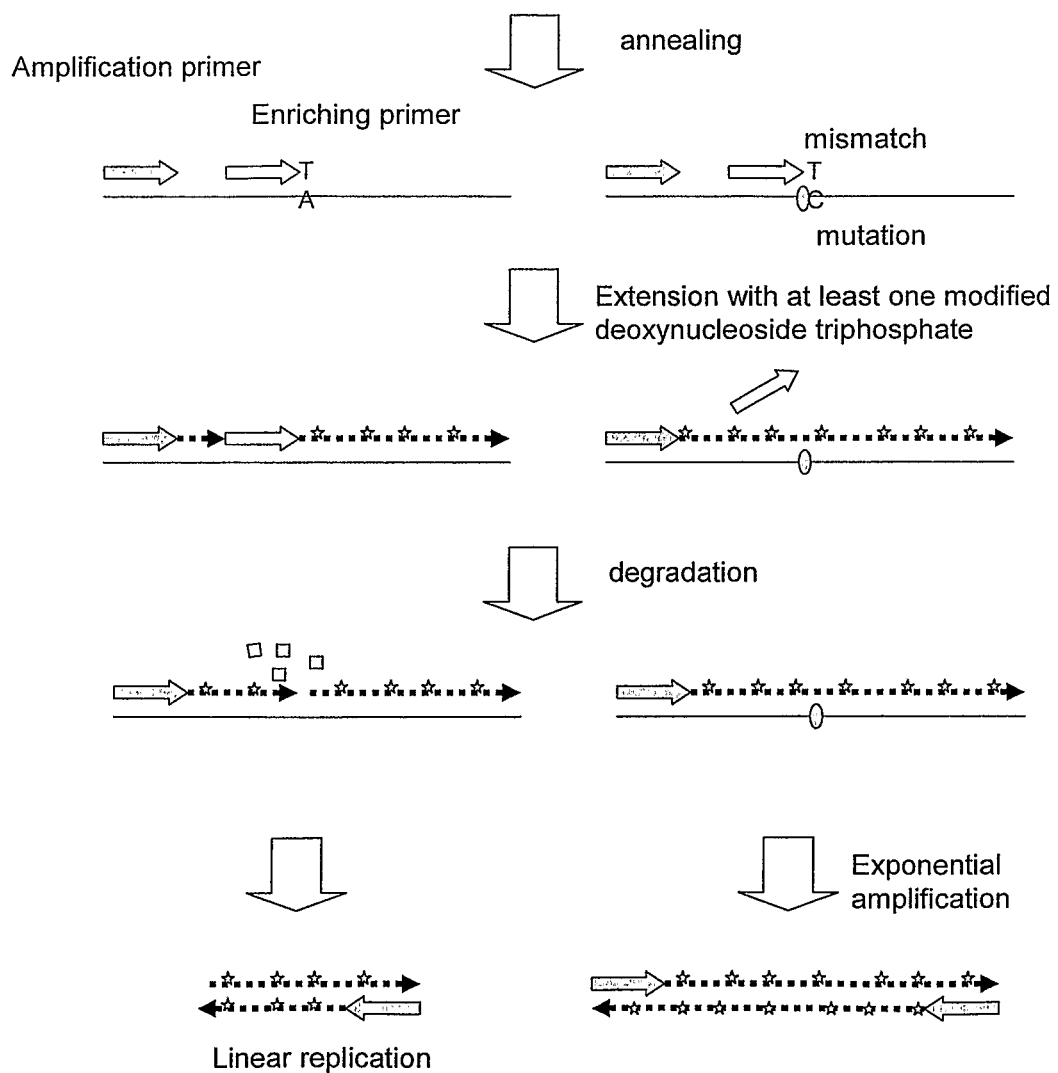
FIG. 4 is a schematic diagram of an embodiment of the present invention showing an enriching primer annealing to a diagnostic region, wherein the 3' terminus nucleotide (T, thymidine) of the enriching primer matches to the normal nucleotide (A, adenosine) and mismatches to the variant nucleotide (C, cytidine) of a diagnostic region of the target sequence.

The enriching primer may be an ordinary oligonucleotide primer made of natural nucleotides and a phosphodiester linkage—in other words, it might not comprise a non-nucleotide, a linkage chemical moiety or modified nucleotides. In this embodiment, a part or whole of the enriching primer is degradable by a nuclease activity. When the enriching primer anneals to the diagnostic region containing the corresponding normal nucleotide on the target sequence, the enriching primer is extended by a DNA polymerase with a 5' exonuclease activity under an extension condition which comprises at least one modified deoxynucleoside triphosphate. A part or whole of the enriching primer is degraded by said 5' exonuclease activity, whereas a part or whole of the extended strand is resistant to cleavage (FIG. 4).

In one embodiment, a given nucleotide variation, for example a point mutation, is enriched and detected by designing the enriching primer to have an appropriate terminal nucleotide which is complementary to the normal nucleotide such that the synthesis of the enriching primer extension product will block the extension of the upstream amplification primer. When the enriching primer anneals to the diagnostic region containing the variant nucleotide, the mismatched 3' end of the enriching primer cannot be extended and the enriching primer will be dissociated from the template under the extension conditions. In this regard reference herein to the "appropriate terminal nucleotide" means the terminal nucleotide of the primer from which, in use, synthesis would be initiated if possible. Thus, since in general the agent for polymerisation would initiate synthesis at the 3' end of the primer, the appropriate terminal nucleotide would in general be the 3' terminal nucleotide. To prevent the 3' terminal nucleotide or other nucleotides of the enriching primer being digested by a nuclease activity, the enriching primer may comprise modified nucleotides or linkages which render the whole or part of the enriching primer resistant to nuclease cleavage. It is preferred that the last 5 nucleotides or linkages at the 3' end and/or 5' end are modified such that the enriching primer is resistant to nuclease cleavage. It is more preferred that the last nucleotide or linkage at 3' end and/or 5' end is modified such that the enriching primer is resistant to nuclease cleavage. Any type of modification which renders the primer resistant to exonuclease cleavage can be used.

Examples include phosphorothioate linkage, methylphosphonate linkage, LNA, PNA, Oligo-2'-OMe-nucleotides or the like.

In another embodiment, a given nucleotide variation is enriched for and detected by designing the enriching primer to have an appropriate terminal nucleotide which is complementary to the suspected variant nucleotide. In this case, the 3' terminal nucleotide of the enriching primer is modified such that it is not suitable for a polymerase extension, whereby the enriching primer which anneals to the diagnostic region containing the suspected variant nucleotide is non-extendable. When the enriching primer anneals to the diagnostic region containing the corresponding normal nucleotide, the mismatched 3' terminal nucleotide of the enriching primer is removed by a proof-reading activity of a nucleic acid polymerase, thereby rendering the enriching primer extendable. In yet another embodiment, the enriching primer has a blocked 3' terminal nucleotide that is complementary to the normal nucleotide on the diagnostic region. The blocked 3' terminal nucleotide is removed by a pyrophosphorolysis activity of an enzyme, preferably a DNA polymerase, when it matches to the normal nucleotide on the template. The blockage of the 3' end of the enriching primer can be achieved by any means known in the art. Blocking moieties are chemical moieties which can be added to a nucleic acid to inhibit nucleic acid polymerization catalyzed by a nucleic acid polymerase. Blocking moieties are typically located at the terminal 3' end of the enriching primer, which is made up of nucleotides or derivatives thereof. For example, by attaching a blocking group to a terminal 3' OH, the 3' OH group is no longer available to accept a nucleoside triphosphate in a polymerization reaction. Numerous different groups can be added to block the 3' end of the enriching primer. Examples of such groups include alkyl groups, non-nucleotide linkers, phosphorothioate, alkane-diol residues, peptide nucleic acid and nucleotide derivatives lacking a 3' OH (e.g., cordycepin, dideoxynucleotide, or acyclonucleotides).

The term "first amplification primer" is used herein to refer to a primer that is capable of hybridising to the target sequence upstream of the enriching primer and is used for amplification. When there are first and second "amplification primers" used in a reaction, the pair of amplification primers amplify a target region spanning the diagnostic region. One "amplification primer" has a nucleotide sequence such that it is capable of hybridising to an extension product of the other amplification primer, after separation from its complement, whereby one primer extension product serves as a template for synthesis of an extension product of another amplification primer. When two different, non-overlapping oligonucleotides anneal to different regions of the same linear complementary nucleic acid sequence, and the 3' end of one oligonucleotide points toward the 5' end of the other, the former may called the "upstream" oligonucleotide and the latter the "downstream" oligonucleotide.

In some embodiments of the present invention, a nucleic acid template capable of forming a stem-loop structure may be created by an extension of a first amplification primer with a 5' tail sequence. The 5' tail sequence comprises nucleotide or non-nucleotide sequence complementary to the binding site of the second amplification primer. In other words, the 5' tail sequence comprises nucleotide or non-nucleotide sequence identical or substantially identical to the sequence of the second primer. The first and second amplification primers are capable of hybridising to the extension product of the second and first amplification primers, respectively. Alternatively, the nucleic acid template capable of forming a stem-loop structure may be created by an extension of first and second amplification primers with the same 5' tail sequence. The 5' tail sequence comprises nucleotide or non-nucleotide sequence complementary to the binding site of a third amplification primer. In other words, the 5' tail sequence comprises nucleotide or non-nucleotide sequence identical or substantially identical to the sequence of the third primer. The third primer may be an arbitrary universal primer unrelated to the target sequence.

The enriching primer or amplification primer may be a labelled oligonucleotide. The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, magnetism, enzymatic activity and the like.

In one embodiment, the present invention is directed to enriching more than one suspected variant nucleotide in the same sample. In this case, more than one enriching primer targeting different SNPs or mutations may be included in a reaction.

B. Probes

As used herein, the term "probe" refers to a labelled oligonucleotide that forms a duplex structure with a sequence in the template nucleic acid, due to complementarity of at least one sequence in the probe with a sequence in the template region. The probe, normally, does not contain a sequence complementary to the sequence(s) used to prime the amplification. But in some embodiments of the present invention, a probe does contain a sequence complementary to a part of a primer. Generally the 3' terminus of the probe will be "blocked" to prohibit incorporation of the probe into a primer extension product. But in some embodiments of the present invention, some probes are also working as primers and therefore are not blocked at the 3' terminus. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as a dideoxynucleotide.

Various probes can be used in conjunction with the present invention. It is preferred that the probe used is a bridge-probe. A bridge-probe comprises at least two binding portions linked by a bridging portion, wherein the first binding portion is capable of hybridising to a first region of a template nucleic acid, and wherein the second binding portion is capable of hybridising to a second region adjacent or substantially adjacent to the first region of the template nucleic acid.

The term "adjacent" or "substantially adjacent" as used herein refers to the positioning of the second binding portion with respect to the first binding portion on its complementary strand of the template nucleic acid. The two template regions hybridised by the first and second binding portions of a bridge-probe may be contiguous, i.e. there is no gap between the two template regions. Alternatively, the two template regions hybridised by the first and second binding portions of a bridge-probe may be separated by 1 to about 200 nucleotides, more preferably, about 1 to 100 nucleotides. Alternatively, when the present method is used in the PCR enrichment and detection methods as taught herein, the "adjacency" may be anywhere within the sequence to be amplified, or anywhere downstream of an amplification primer.

The first region of a template nucleic acid may be a region of interest on a target nucleic acid, which may be a diagnostic region with suspected variant nucleotides (FIGS. 6A, B, C, D). Alternatively, the first region of a template nucleic acid may be a region on a primer extension product, wherein the second region is a part of a primer or a probe (FIGS. 6G, H). In another aspect, the first region of a template nucleic acid and the second region of a template nucleic acid may both parts of a primer or a probe (FIG. 6I).

The bridging portion is located on the probe between the binding portions. The bridging portion may comprise a nucleotide or non-nucleotide chemical moiety and can be any length. However, for a given gap distance between the first region and the second region of the template nucleic acid, the length and/or composition of the bridging portion is capable of regulating the Tm of the individual binding portion and/or the Tm of the bridge-probe as a linked molecule. Melting Temperature (Tm), by definition, is the temperature at which one half of the DNA duplex will dissociate to become single stranded, and indicates the duplex stability. It is advantageous for the bridging portion to include some non-nucleotide chemical moieties which are not suitable as templates for a DNA polymerase, thereby reducing non-specific priming. Some chemical moieties may also be more flexible, i.e. may not be as rigid as natural nucleotide linkages, and therefore are easy to fold and may increase the actual Tm for the low Tm binding portion. Such non-nucleotide moieties may include, but are not limited to, HEG, non-nucleotide linkage, nucleotide derivatives or analogs, or a dye. The bridging portion not only links two binding portions, but regulates the binding characteristics of the bridge-probe, especially the binding portion of the bridge-probe with a low individual Tm. Normally, the two binding portions are considered as separate molecules as one binding portion has a higher Tm than another binding portion. The length of the bridging portion will affect the temperature at which the binding portion, especially the binding portion with the lower Tm, anneals to or dissociates from the template. Depending on the distance between the two regions of the template nucleic acid hybridised by the two binding portions of a bridge-probe, the bridge-probe as a linked molecule, as well as the binding portion when considered individually, generally has a higher Tm when the length of the bridging portion is close in length to the distance between the two template regions hybridised by the two binding portions of a bridge-probe. This rule may only apply when the distance between the two template regions hybridised by the two binding portions of a bridge-probe is not very long, and may not be longer than 200 nucleotides. For this purpose, the length of the bridging portion can range between 0 to 200 nucleotides or equivalent, more preferably, about 1 to 100 nucleotides or equivalent.

The binding portions attached to the ends of the bridging portion are designed to form a specific and stable hybrid with a specific sequence of a template nucleic acid. The binding portion can be any length desired, generally 2 to 60 nucleotides long is preferred, and 6 to 40 nucleotides long is most preferred. The binding portion can comprise nucleotides, nucleotide derivatives, analogs, or non-nucleotide chemical moieties.

The binding portions may be complementary to a specific target nucleic acid sequence and may be designed to be specific to a particular variant at a locus. It is preferred that at least one binding portion (the first binding portion) is complementary to a diagnostic region where a suspected variant nucleotide is located. It is also desirable that two or more binding portions are complementary to multiple diagnostic regions each of which comprises a variant nucleotide.

In the practice of the invention, the different binding portions of a bridge-probe may be annealed to a complementary nucleic acid simultaneously. Alternatively, each binding portion may be designed to have distinct hybridisation properties, especially when hybridising to matched or mismatched target nucleic acid. To best understand the concept of this invention, two melting temperatures (Tm) are assigned to each binding portion: Tm-s is the melting temperature when considering each binding portion as a separate oligonucleotide; Tm-p is the actual melting temperature when the binding portions in a bridge-probe are considered as a linked molecule, i.e. in a real situation the binding portion hybridises to a matched target nucleic acid at the Tm-p. For a given sequence of a binding portion, its Tm-s is constant and is not changed, whereas its Tm-p is partly dependent on the length and/or composition of the bridging portion. With an appropriate bridging portion, a binding portion's Tm-p is usually greater than its Tm-s. This can be very useful for detecting point mutations or single nucleotide differences.

In one embodiment, while the first binding portion hybridises to a diagnostic region with a suspected variant nucleotide, the second binding portion hybridises to a nearby region with respect to the diagnostic region. It is designed that the Tm-s of the second binding portion is greater than the Tm-s of the first binding portion. The knowledge of designing oligonucleotides with different Tm is well known in the art. For example, a longer oligonucleotide with a high G/C content can have a high Tm. Since the second binding portion has a high Tm-s, it will anneal to the target nucleic acid first and at a high annealing temperature. Due to linking of the first binding portion to the second binding portion by an appropriate bridging portion, the Tm-p of the first binding portion is greater than its Tm-s. For example, if a second binding portion of a bridge-probe has a Tm-s of 65° C., the first binding portion of the bridge-probe has a low Tm-s of 36° C. In reality the Tm-p of the first binding portion may be 55° C. Normally, as the first binding portion has a low Tm-s, it can be short in length. It is advantageous to design the first binding portion to be short in length, resulting in a low Tm-s, but the Tm-p will be high. Unlike other probe designs, in which the probe may have an appropriate high Tm but may lose or have limited ability to distinguish a single nucleotide difference, the present design has a great power to distinguish between single nucleotide differences. The first binding portion hybridises to matched and mismatched diagnostic regions at a widely different Tm-p, which can be easily observed. Following the above example, the first binding portion may hybridise to a matched diagnostic region at 55° C., whereas it may hybridise to mismatched diagnostic region at 50° C., differences in temperature which are easily distinguishable.

Modifications of the probe that may facilitate probe binding include, but are not limited to, the incorporation of positively charged or neutral phosphodiester linkages in the probe to decrease the repulsion of the polyanionic backbones of the probe and target (see Letsinger et al., 1988, J. Amer. Chem. Soc. 110:4470); the incorporation of alkylated or halogenated bases, such as 5-bromouridine, in the probe to increase base stacking; the incorporation of ribonucleotides into the probe to force the probe:target duplex into an "A" structure, which has increased base stacking; and the substitution of 2,6-diaminopurine (amino adenosine) for some or all of the adenosines in the probe; the incorporation of nucleotide derivatives such as LNA (locked nucleic acid), PNA (peptide nucleic acid) or the like.

The two binding portions linked by the bridging portion can exist in various orientations. One end of the bridging portion may be attached to the 5' end of the first binding portion, and another end of the bridging portion may be attached to the 3' end of the second binding portion (FIGS. 6A, C and D). In another embodiment, one end of the bridging portion may be attached to the 5' end of the first binding portion, and another end of the bridging portion may be attached to the 5' end of the second binding portion. Alternatively, one end of the bridging portion may be attached to the 3' end of the first binding portion, and another end of the bridging portion may be attached to the 3' end of the second binding portion (FIG. 6B).

The binding portions of the bridge-probe can hybridise to a template nucleic acid in such different ways that the ends of the binding portions may point in different directions. In one embodiment, the ends of a bridge-probe point towards each other when the bridge-probe hybridises to a template nucleic acid. This form of hybridisation may bring two ends of the bridge-probe into close proximity (FIG. 6A). In another embodiment, the ends of a bridge-probe point away from each other when the bridge-probe hybridises to a template nucleic acid (FIGS. 6C and D). In a further embodiment, the ends of a bridge-probe point in the same direction when the bridge-probe hybridises to a template nucleic acid (FIG. 6B).

In one embodiment, the second binding portion of a bridge-probe is complementary to a part of a primer, whereas the first binding portion is complementary to a part of a sequence on the extension strand of the primer. The 3' end of the second binding portion and an appropriate position of the primer are labelled with an interactive label pair such that upon hybridisation of the bridge-probe with the primer extension strand the two labels are in FRET or contact quenching relationship (FIGS. 6G, H). The label on the primer can be located anywhere as long as it interacts with the label on the bridge-probe. In another embodiment, the second binding portion of a bridge-probe is complementary to the 5' part of a the primer/ the second probe, whereas the first binding portion is complementary to the 3' part of the primer/the second probe. The 3' end of the second binding portion and the 5' end of the primer/the second probe are labelled with an interactive label pair (FIG. 6I). In this embodiment, when the primer or the second probe hybridises to a target nucleic acid, the bridge-probe will partly or fully dissociate from the primer or the second probe, thereby generating detectable signals. It is preferred, in this embodiment, that the template regions of the primer or the second probe hybridised by the binding portions of the bridge-probe are arbitrary sequences and can be designed to be constant among different primers or probes. Therefore, the bridge-probe binding to the primers or the second probes can be a universal probe that can be shared by a set of primers or second probes.

In another embodiment, a set of bridge-probes is provided for scanning unknown mutations. Multiple bridge-probes are designed to cover the whole region of interest on a target nucleic acid sequence. Each bridge-probe may be labelled with different dyes. The melting properties of the bridge-probe hybridising to the target nucleic acid are compared to the melting properties of bridge-probes hybridised to normal target and a target suspected to contain mutations (FIG. 8).

It is preferred that a bridge-probe comprises detection labels. The labels produce detectable signals during hybridisation of the probe to a target nucleic acid or during dissociation of the probe from a target nucleic acid. A bridge-probe may comprise a single label; alternatively a bridge-probe may comprise a first label and a second label (FIG. 6 A, B, C). A bridge-probe and its interactive primer/probe may comprise a first label and second label, respectively (FIGS. 6E, F, G, H, I).

In one embodiment, the first binding portion is attached with a first label, the second binding portion is attached with a second label, wherein said first label and second label are contact quenching pairs, wherein one of the labels is a quencher, wherein upon hybridization of the probes with the target sequence the first and second labels are in a contact quenching relationship.

In another embodiment, the first binding portion is attached with a first label, the second binding portion is attached with a second label, wherein said first label and second label are fluorescence energy transfer pairs, wherein upon hybridization of the probes with the target sequence the first and second labels are in a fluorescence resonance energy transfer relationship (FRET).

In yet another embodiment, a bridge-probe may need to work together with another oligonucleotide probe or primer as depicted in FIGS. 6E, 6G, 6H and 6I. In FIG. 6E, a bridge-probe and another probe hybridise to adjacent regions of the target sequence, one of the probes being labelled with a fluorophore and the other probe labelled with a quencher of a FRET or contact quenching pair such that upon hybridization of the probes with the amplified products the fluorophore and quencher are in a contact quenching relationship, wherein the fluorophore and quencher are within 5 nucleotides of one another. In FIGS. 6G and 6H, an amplification reaction contains amplification primers and a bridge-probe, wherein one of said amplification primers and the probe are each labelled with one member of a fluorophore and a quencher such that upon hybridization of the probes with the amplified products the fluorophore and quencher are in a contact quenching relationship, wherein the labelled probe hybridizes to an amplified copy of the target nucleic acid sequence within 5 nucleotides of the labelled primer or the labelled probe hybridizes to the target nucleic acid sequence and a part of the labelled primer.

It has been known that in homogeneous hybridization assays, two interactive fluorophores can be attached to the ends of two different oligodeoxyribonucleotide probes or to the two ends of the same oligodeoxyribonucleotide probe. A target nucleic acid reveals itself by either bringing the donor fluorophore and the acceptor fluorophore close to each other, permitting energy transfer between them to occur, or by separating them from each other, precluding the transfer of energy (Marras S. A. E. et al 2002, Nucleic Acids Res. 30(21)). The earliest formats for homogeneous hybridization assays utilized a pair of oligodeoxyribonucleotide probes labelled at their respective 5' and 3' ends that were designed to bind to adjacent sites on a target strand, thereby bringing a donor and acceptor moiety close to each other (Patent no. EPO070685 and Cardullo R. A. et al 1988). A second approach utilizes a pair of mutually complementary oligodeoxyribonucleotides, in which one of the oligodeoxyribonucleotides serves as a probe for a single-stranded target sequence. The 5' end of one oligodeoxyribonucleotide is labelled with a donor fluorophore and the 3' end of the other oligodeoxyribonucleotide is labelled with an acceptor fluorophore, such that when the two oligodeoxyribonucleotides are annealed to each other, the two labels are close to one another. Since small complementary oligodeoxyribonucleotides bind to each other in a dynamic equilibrium, target strands compete for binding to the probe, causing the separation of the labelled oligodeoxyribonucleotides (Morrison L. E. et al 1989, Anal. Biochem., 183: 231-244)). In a third approach, the donor and acceptor fluorophores are attached to the ends of the same oligodeoxyribonucleotide, which serves as the probe. Since an oligodeoxyribonucleotide in solution behaves like a random coil, its ends occasionally come close to one another, resulting in a measurable change in energy transfer. However, when the probe binds to its target, the rigidity of the probe-target helix keeps the two ends of the probe apart from each other, precluding interaction between the donor and the acceptor moieties (Parkhurst K. M. and Parkhurst, L. J. 1995, Biochemistry, 34: 285-292). In the fourth approach, single-stranded oligodeoxyribonucleotides called molecular beacons possess short additional sequences at either end of a probe sequence that are complementary to one another, enabling terminal labels to be in close proximity through the formation of a hairpin stem. Binding of this probe to its target creates a relatively rigid probe-target hybrid that causes the disruption of the hairpin stem and the removal of the donor moiety from the vicinity of the acceptor moiety, thus restoring the fluorescence of the donor (Tyagi S, and Kramer, F. R. 1996, Nat. Biotechnol., 14: 303-308). In addition to these hybridization-based schemes and their variations, dual-labelled randomly coiled probes that bind to template strands during PCR, can be enzymatically cleaved by the endonuclease activity of DNA polymerase ("TaqMan"™ probes), separating the donor and acceptor moieties and enabling nucleic acid synthesis to be monitored in real time (Heid C. A., Stevens, J., Livak, K. J. and Williams, P. M. 1996, Genome Res., 6: 986-994).

If an acceptor fluorophore is brought closer to a donor fluorophore within the range 20-100 □, the fluorescence intensity of the acceptor fluorophore increases, whereas the fluorescence intensity of the donor fluorophore decreases. This is due to an increase in the efficiency of fluorescence resonance energy transfer (FRET) from the donor to the acceptor fluorophore. However, if the two moieties are brought any closer, the fluorescence intensities of both the donor and the acceptor fluorophores are reduced. At these intimate distances, most of the absorbed energy is dissipated as heat and only a small amount of energy is emitted as light, a phenomenon sometimes referred to as static or contact quenching (Lakowicz J. R. 1999, Principles of Fluorescence Spectroscopy. Kluwer Academic/Plenum Publishers, New York, N.Y.).

In adjacent probes and in randomly coiled probes, the donor and the acceptor moieties remain at such a distance from each other that FRET is the predominant mechanism of quenching. On the other hand, when competitive hybridization probes and molecular beacons are not hybridized to targets, the two moieties are very close to each other and contact quenching is the predominant mechanism of quenching. One of the useful features of contact quenching is that all fluorophores are quenched similarly, regardless of whether the emission spectrum of the fluorophore overlaps the absorption spectrum of the quencher, one of the key conditions that determines the efficiency of FRET (Tyagi S., Bratu, D. P. and Kramer, F. R. 1998, Nat. Biotechnol., 16: 49-53).

A further simplification of homogeneous assays that utilize fluorescently labelled probes is the use of non-fluorescent dyes as acceptors or quenchers. Quenching by non-fluorescent dyes enables changes in the intensity of fluorescence to be measured directly, rather than as an alteration in the shape of the emission spectrum, which is more difficult to monitor. This improvement has also led to a higher degree of multiplexing, as the part of the spectrum that would have been occupied by the fluorescence of the quencher can instead be reserved for the fluorescence of additional fluorophores for the detection of more targets (Marras S. A., Kramer, F. R. and Tyagi, S. 1999, Genet. Anal., 14: 151-156).

Recently, a number of unique non-fluorescent quenchers, ranging from nucleotides to gold particles, have been introduced for use in fluorogenic probes (Dubertret B., Calame, M. and Libchaber, A. J. 2001, Nat. Biotechnol., 19: 365-370). Quenching efficiencies up to several thousand-fold have been reported for some of these quenchers.

In the prior art discussed above, researchers have mainly used approaches that depend on detecting increased fluorescence of the labels upon hybridisation of probe to target sequence. FRET is the main mechanism behind these approaches. The hybridization probes (U.S. Pat. No. 6,174,670) uses two fluorescent dyes which are dependent on FRET effect. This approach limits the number of multiple targets which can be detected in a single reaction.

In the present invention, the inventor has found that detection of decreased fluorescence of the labels due to contact quenching upon hybridisation of probe to the target sequence is more sensitive than FRET. In one embodiment of the present invention, an amplification reaction contains amplification primers and a nucleic acid probe, wherein one of said amplification primers and the probe are each labelled with one member of a fluorophore and a quencher such that upon hybridization of the probes with the amplified products the fluorophore and quencher are in a contact quenching relationship. One of the nucleic acid probes may be a bridge-probe.

In another embodiment of the invention, wherein an amplification reaction contains amplification primers and two nucleic acid probes that hybridize to adjacent regions of the target sequence, one of said probes being labelled with a fluorophore and the other probe labelled with a quencher of a contact quenching pair such that upon hybridization of the probes with the amplified products the fluorophore and quencher are in a contact quenching relationship, wherein the fluorophore and quencher are within 5 nucleotides of one another. One of the nucleic acid probes may be a bridge-probe.

It is preferred that for effective contact quenching, the fluorophores and quencher are at a distance of about 0-10 nucleotides. It is more preferred that the fluorophores and quencher are at a distance of about 0-5 nucleotides. It is most preferred that the fluorophores and quencher are at a distance of about 0-2 nucleotides. The quencher is preferably a non-fluorescent entity. The quencher may be a nanoparticle. A nanoparticle may be a gold nanoparticle. It is also possible that the quencher is a G residue or multiple G residues.

In the above embodiments, the labels may be interactive fluorophores or non-fluorophore dyes or any entity. One example of such interactive labels is a fluorophore-quencher pair. "Fluorophore" as used herein to refer to moieties that absorb light energy at a defined excitation wavelength and emit light energy at a different defined wavelength. Examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red and Texas Red-X.

As used herein, the term "quencher" includes any moiety that is capable of absorbing the energy of an excited fluorescent label when it is located in close proximity to the fluorescent label and capable of dissipating that energy. A quencher can be a fluorescent quencher or a non-fluorescent quencher, which is also referred to as a dark quencher. The fluorophores listed above can play a quencher role if brought into proximity to another fluorophore, wherein either FRET quenching or contact quenching can occur. It is preferred that a dark quencher which does not emit any visible light is used. Examples of dark quenchers include, but are not limited to, DABCYL (4-(4'-dimethylaminophenylazo) benzoic acid) succinimidyl ester, diarylrhodamine carboxylic acid, succinimidyl ester (QSY-7), and 4',5'-dinitrofluorescein carboxylic acid, succinimidyl ester (QSY-33), quencherl, or "Black hole quenchers" (BHQ-1, BHQ-2 and BHQ-3), nucleotide analogs, nucleotide G residues, nanoparticles, and gold particles.

C. Nucleoside Triphosphate

The term "nucleoside triphosphate" is used herein to refer to nucleosides present in either DNA or RNA and thus includes nucleosides which incorporate adenine, cytosine, guanine, thymine and uracil as base, the sugar moiety being deoxyribose or ribose. In general deoxyribonucleosides will be employed in combination with a DNA polymerase. It will be appreciated however that other modified bases capable of base pairing with one of the conventional bases adenine, cytosine, guanine, thymine and uracil may be employed. Such modified bases include for example 8-azaguanine and hypoxanthine.

The term "nucleotide" as used herein can refer to nucleotides present in either DNA or RNA and thus includes nucleotides which incorporate adenine, cytosine, guanine, thymine and uracil as base, the sugar moiety being deoxyribose or ribose. It will be appreciated, however, that other modified bases capable of base pairing with one of the conventional bases, adenine, cytosine, guanine, thymine and uracil, may be used in the primers employed in the present invention. Such modified bases include for example 8-azaguanine and hypoxanthine.

In one embodiment of the invention, wherein a DNA polymerase with 5' exonuclease activity is used, the extension condition comprises all four deoxynucleoside triphosphates, at least one of which is substituted (or modified). The substituted deoxynucleoside triphosphate should be modified such that it will inhibit cleavage by the 5' exonuclease of the DNA polymerase. Examples of such modified deoxynucleoside triphosphates can include 2'-deoxyadenosine 5'-O-(1-thiotriphosphate), 5-methyldeoxycytidine 5'-triphosphate, 2'-deoxyuridine 5'-triphosphate and 7deaza-2'-deoxyguanosine 5'-triphosphate.

D. Enzyme

The disclosed methods make use of nucleic acid polymerase for primer extension. Any nucleic acid polymerase can be used. In some embodiments, wherein the extension of the enriching primer blocks the extension initiated from the amplification primer, the polymerases used preferably do not have a strand displacement activity, such as Taq DNA polymerase or the Stoffel fragment of the Taq polymerase. In other embodiments, wherein the enriching primer comprises a 3' blocking moiety which, if not removed, prevents primer extension, the DNA polymerase comprises a proof-reading activity or pyrophosphorolysis activity, such as Pfu, PWO, Pfx, Vent DNA polymerases, AmpliTaqFS or ThermoSequenase. In other embodiments, wherein the extension of the enriching primer promotes the hybridisation and extension of the amplification primer, the polymerases used preferably have a strand displacement activity or a 5' to 3' exonuclease activity, such as Vent (exo-) polymerase, Taq polymerase. It is particularly preferred that the DNA polymerase is a thermostable DNA polymerase.

II Method

Prior art methods (U.S. Pat. No. 5,891,625) use oligos of nucleotide analogues, such as PNAs or LNAs, which hybridise strongly to the nucleic acids to inhibit nucleic acid amplification procedures. The methods of the present invention are simple to perform in the light of the present disclosure, and are highly specific. In certain embodiments claimed herein, the enriching primer anneals to the diagnostic region and is extended only when the diagnostic region of the target sequence contains a particular nucleotide. In one embodiment, the enriching primer extension product specifically blocks the extension initiated from an upstream primer, thereby preventing amplification of the target region containing the particular nucleotide, whereas the target region containing the variant nucleotide is exponentially amplified. In another embodiment, the extension of the enriching primer opens up a stem-loop structure of the template, allowing the amplification primer to anneal and extend. The amplification uses a pair of amplification primers that anneal to the target sequence outside of the diagnostic region, whereas some previous methods use amplification primers that directly anneal to the diagnostic region, wherein PCR errors are often misinterpreted as a positive result for the presence of rare mutations. Additionally, the amplification product in the present invention is enriched for the desired target nucleic acid, which can be reliably typed and analysed by the bridge-probe provided in the present invention or by any other method, such as real-time PCR, DNA sequencing and the like.

It should be appreciated that whilst the method of the present invention is of particular interest in enriching and detecting the diagnostic region of target nucleic acids containing point mutations, the method is equally applicable to enriching and detecting a diagnostic region with deletions and insertions, including deletions and insertions of more than one nucleotide. The present invention is also valuable for enriching target regions containing substitutions of more than one nucleotide. In this regard it is simply necessary to know the relevant nucleotides so that the necessary enriching primer(s) may be designed appropriately. Thus "variant nucleotide" as used herein will be understood not just to be a substitution, but also potentially an insertion or deletion, with the required complementarity (e.g. of probe or primer) being adjusted accordingly.

One method of the invention is provided for enriching and/or detecting a target nucleic acid with at least one variant nucleotide from a nucleic acid population in a sample, said method comprising:
(a) treating the nucleic acid population with an enriching primer and an amplification primer for a first strand of a nucleic acid template containing the target nucleic acid sequence to create a mixture of duplexes (between the primer or primers, and the target nucleic acid having the variant or normal nucleotides), wherein the enriching primer and amplification primer are capable of annealing to the template in the positions such that the 3' end of the amplification primer is upstream of (generally adjacent or substantially adjacent) to the 5' end of the enriching primer, wherein the nucleotide sequence of said enriching primer is such that it is substantially complementary to a diagnostic region where the suspected variant nucleotide is located, wherein said duplex comprises the enriching primer and amplification primer annealed to the template or comprises the enriching primer annealed to the template;
(b) maintaining the mixture of step (a) under extension conditions, which comprise appropriate nucleoside triphosphates and a nucleic acid polymerase, to extend the annealed primers, if extendable, to synthesize primer extension products.

As described below, in one embodiment the annealed enriching primer is not extendable when it anneals to the diagnostic region containing the suspected variant nucleotide but the annealed enriching primer is extended to synthesize the enriching primer extension product when it anneals to the diagnostic region containing the corresponding normal nucleotide, wherein the extension of the enriching primer either blocks the extension of the amplification primer or promotes the hybridisation and extension of the amplification primer. More specifically, in step (a) both the enriching primer and amplification primer anneal to the nucleic acid template, and in step (b) the annealed enriching primer is not extendable when it anneals to the diagnostic region containing the suspected variant nucleotide, whereby the enriching primer is dissociated from the target sequence under the extension condition, thereby allowing extension of the amplification primer to pass through the diagnostic region containing the suspected variant nucleotide, wherein the annealed enriching primer is extended to synthesize the enriching primer extension product when it anneals to the diagnostic region containing the corresponding normal nucleotide, whereby the extension of the amplification primer is blocked by the extension product of the enriching primer.

In another embodiment, in step (a) the nucleic acid template forms a stem-loop structure under hybridisation conditions, wherein the double-stranded stem comprises an amplification primer binding site, the loop comprises the target nucleic acid sequence, wherein the enriching primer anneals to the diagnostic region in the loop, wherein in step (b) the enriching primer is extended when it anneals to the diagnostic region with a variant nucleotide, this extension opens up the stem loop structure thereby allowing the amplification primer to anneal to the primer binding site and promoting amplification, wherein the enriching primer is not extendable when it anneals to the diagnostic region with a normal nucleotide, whereby the stem-loop structure is intact and prevents an amplification primer, from annealing to the primer binding site. In this embodiment, the method further comprises: step (c), treating the mixture of step (b) under hybridisation conditions allowing the amplification primer to anneal to the primer binding site of the opened stem-loop template, and step (d) maintaining the mixture of step (c) under extension conditions to extend the annealed amplification primer, wherein said extension conditions comprise appropriate nucleotide triphosphates, a nucleic acid polymerase, and an agent with strand displacement activity or an agent with 5' to 3' exonuclease activity, wherein said strand displacement activity allows the extension product of enriching primer to be displaced, wherein said 5' to 3' exonuclease activity allows the extension product of enriching primer to be degraded. The degradation of the enriching primer extension product may result in generating detection signals due to labels on the enriching primer or nucleoside triphosphates. It is preferred that steps (a) to (d) are repeated in an amplification reaction which may be a PCR or isothermal amplification. The strand displacement activity is preferably provided by the polymerase. The 5' to 3' exonuclease activity is preferably provided by the polymerase.

The enriching primer may comprise a moiety that renders the extension product of the enriching primer unsuitable for exponential amplification. In some embodiments, the nucleic acid polymerase used can be a DNA polymerase with or without a proof-reading activity. If a DNA polymerase with a proof-reading activity is used, the enriching primer may comprise modified nucleotides or linkages, especially the 3' terminus nucleotide or linkage, so that the enriching primer is resistant to nuclease cleavage. The enriching primer may be an ordinary oligonucleotide primer made of natural nucleotides and phosphodiester linkages—in other words; it may not comprise a chemical moiety or modified nucleotides. In this embodiment, a part or whole of the enriching primer is degradable by a nuclease activity. When the enriching primer anneals to the diagnostic region containing the corresponding normal nucleotide on the target sequence, the enriching primer is extended by a DNA polymerase containing a 5' exonuclease activity under an extension condition comprising at least one modified deoxynucleoside triphosphate. A part or whole of the enriching primer is degraded by said 5' exonuclease activity, whereas a part or whole of the extended strand is resistant to cleavage.

Another method of the invention is provided which comprises:
(a) treating the nucleic acid population with a first enriching primer and a first amplification primer for a first strand of a target nucleic acid sequence to create a mixture of duplexes comprising the enriching primer and amplification primer annealed to the target nucleic acid under hybridisation conditions, wherein the nucleotide sequence of said enriching primer is such that it is substantially complementary to the diagnostic region where the suspected variant nucleotide is located, wherein a 3' terminal nucleotide of the enriching primer is complementary to the suspected variant nucleotide, the 3' terminal nucleotide of the enriching primer is modified such that it is not suitable for polymerase extension, whereby the enriching primer that anneals to the diagnostic region containing the suspected variant nucleotide is non-extendable, wherein when the enriching primer anneals to the diagnostic region containing the corresponding normal nucleotide, the mismatched 3' terminal nucleotide of the enriching primer is removed by a proof-reading activity of a nucleic acid polymerase, thereby rendering the enriching primer extendable, wherein the duplexes comprise the target nucleic acid annealed to the enriching primer and the amplification primer such that the 3' end of the amplification primer is adjacent to or upstream of the 5' end of the enriching primer; (b) maintaining the mixture of step (a) under extension conditions, which comprise appropriate nucleoside triphosphates and a nucleic acid polymerase with a proof-reading activity to extend the annealed primers, if extendable, to synthesize primer extension products, wherein the annealed enriching primer is not extendable when it anneals to the diagnostic region containing the suspected variant nucleotide because of the blocked 3' end, whereby the enriching primer is dissociated from the target sequence under the extension conditions, which may have a temperature higher than that used for the hybridising conditions, thereby allowing extension of the amplification primer to pass through the diagnostic region containing a suspected variant nucleotide, wherein when the annealing primer anneals to the diagnostic region containing the corresponding normal nucleotide, the mismatched 3' terminus nucleotide is removed, therefore is extended to synthesize the enriching primer extension product, whereby the extension of the amplification primer is blocked by the enriching primer extension product.

In a further embodiment of the present invention, an enriching primer comprises a blocked 3' terminal nucleotide that is a match for the normal nucleotide, whereas it is a mismatch for the variant nucleotide of the diagnostic region. The annealed enriching primer is extended on the template of the target sequence containing the appropriate normal nucleotide after the terminal nucleotide of the primer is removed by a pyrophosphorolysis activity of a DNA polymerase, wherein the enriching primer extension product blocks extension of an upstream amplification primer. The annealed enriching primer is not extended on the template containing the variant nucleotide and is dissociated from the template, allowing the extension of an upstream amplification primer to pass through the diagnostic region. The enriching primer extension product can be partially copied in a linear manner, whereas the amplification primer extension product can be amplified exponentially.

In another method of the invention, the enriching primer may comprise a tail sequence of nucleotides or non-nucleic acid 5' to the priming portion of the enriching primer, wherein the 5' tail sequence is complementary or substantially complementary to a primer binding site on the enriching primer extension product. Upon denaturation and hybridisation, the enriching primer extension product folds back to form a stem-loop structure that blocks the binding site for the second amplification primer, whereas the amplification primer extension product can be amplified exponentially.

A further method of the invention comprises: (a) treating the sample with a first enriching primer and a first amplification primer for a first strand of a target nucleic acid sequence, and a bridge-probe and second amplification primer for a second strand of the target nucleic acid sequence that is complementary to the first strand of the target nucleic acid, to create a mixture of duplexes comprising the enriching primer and amplification primer annealed to the target nucleic acid under hybridisation conditions, wherein the nucleotide sequence of said enriching primer is such that it is substantially complementary to the diagnostic region on the first strand of the target nucleic acid where the suspected variant nucleotide is located, wherein the first binding portion of the bridge-probe is substantially complementary to the diagnostic region on the second strand of the target nucleic acid; (b) maintaining the mixture of step (a) under extension conditions, which comprise appropriate nucleoside triphosphates and a nucleic acid polymerase to extend the annealed primers, if extendable, to synthesize primer extension products, wherein the annealed enriching primer is not extendable when it anneals to the diagnostic region containing the suspected variant nucleotide, whereby the enriching primer is dissociated from the target sequence under the extension conditions, which may have a temperature higher than that used for hybridisation conditions, thereby allowing extension of the amplification primer to pass through the diagnostic region containing a suspected variant nucleotide, wherein the annealed enriching primer is extended to synthesize the enriching primer extension product when it anneals to the diagnostic region containing the corresponding normal nucleotide, whereby the extension of the amplification primer is blocked by the enriching primer extension product.

The above method may further comprise repeating steps (a) and (b) in an amplification method. Any amplification system can be used to include these steps, such as PCR, SDA, LAMP, 3SR and the like. PCR is a preferred amplification method to incorporate these steps.

In either method described herein, a sample is provided which is suspected to contain the target nucleic acid and the nucleotide variant of interest. The target nucleic acid contained in the sample may be double-stranded genomic DNA or cDNA if necessary, which is then denatured, using any suitable denaturing method including physical, chemical, or enzymatic means that are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as single-stranded RNA or DNA viruses.

The denatured nucleic acid strands are then incubated with oligonucleotide primers under hybridisation conditions; conditions that enable the binding of the primers to the single nucleic acid strands. The enriching primer anneals to the diagnostic region and may or may not be extended. The amplification primer anneals to the nucleic acid strand upstream of the enriching primer and, when extended, passes through the diagnostic region or its extension is blocked by the enriching primer extension product. In one aspect, a reaction includes a first amplification primer and a first enriching primer annealing to the first strand of the target sequence, and a second amplification primer annealing to the second strand of the target sequence, which is complementary to the first strand of the target sequence. In another aspect, a reaction includes a first amplification primer and a first enriching primer annealing to the first strand of the target sequence, and a second amplification primer and a second enriching primer annealing to the second strand of the target sequence, which is complementary to the first strand of the target sequence.

In one embodiment, the nucleic acid template forms a stem-loop structure. The nucleic acid template capable of forming a stem-loop structure may be created by an extension of a first amplification primer on the target nucleic acid in the sample. The first amplification primer comprises a 5' tail sequence, which comprises nucleotide or non-nucleotide sequence complementary to the binding site of second amplification primer. The first and second amplification primers are capable of hybridising to the extension product of the second and first amplification primers, respectively, after separation from its complement or from the stem-loop structure. The nucleic acid template may be created by extensions of both first and second amplification primers on the target nucleic acid in the sample. In another embodiment, both first and second amplification primers comprise the same 5' tail sequence, wherein said 5' tail sequence comprises nucleotide or non-nucleotide sequence complementary to the binding site of a third amplification primer. The third amplification primer is present at concentrations that greatly exceed the concentrations of the first and second amplification primers in the reaction. The third amplification primer may be present in the reaction at a concentration of least 2 times more than the concentration of the first and second amplification primers. Preferably, the third amplification primer may be present in the reaction at a concentration of at least 3 times more than the concentration of the first and second amplification primers.

The amplification primers are selected so that their relative positions along a duplex sequence are such that an extension product synthesized from the first amplification primer, when the extension product is separated from its template (complement), serves as a template for the extension of the second amplification primer.

In the practice of the invention, the enriching primer must first be annealed to a complementary nucleic acid before the amplification primer extension blocks the enriching primer binding site. To achieve this, a variety of techniques may be employed. One can position the enriching primer so that the 5' end of the enriching primer is relatively far from the 3' end of the amplification primer, thereby giving the enriching primer more time to anneal. One can also use an enriching primer with a higher Tm than the amplification primer. For example, the enriching primer can be designed to be longer than the amplification primer. The nucleotide composition of the enriching primer can be chosen to have greater G/C content and, consequently, greater thermal stability than the amplification primer. In a similar fashion, one can incorporate into the enriching primer modified nucleotides which contain base analogues that form more stable base pairs than the bases that are typically present in naturally occurring nucleic acids.

The thermocycling parameters can also be varied to take advantage of the differential thermal stability between the enriching primer and amplification primers. For example, following the denaturation step in thermocycling, an intermediate temperature may be introduced which is permissible for enriching primer binding but not for amplification primer binding; the temperature is then increased to the extension temperature (for example 72° C.), whereby permitting extension of the matched enriching primer and melting away of unextended enriching primer. The cycles of an intermediate temperature and extension temperature can be repeated as many times as desirable to allow the matched enriching primer to extend on as many target templates as possible. The temperature can then be reduced to permit amplification primer annealing and extension.

In some embodiments of the present invention, the enriching primer extension product functions as a blocker of an upstream primer extension and preferably is not being used as a template for amplification; a non-copiable moiety incorporated in the enriching primer that will block replication of part or whole of the enriching primer can be used and is preferred. In principle, the non-copiable moiety (blocking moiety) included in the enriching primer may be any entity which is not recognized as a suitable template by a polymerase. It is desirable that the blocking moiety (for example dR-biotin, dR-amine) is capable of insertion in synthetic oligonucleotides by incorporation of appropriate precursors (e.g. phosphoramidites) during in vitro synthesis of the oligonucleotide.

Template-dependent extension of the oligonucleotide primer(s) is catalyzed by a polymerizing agent in the presence of adequate amounts of the four deoxyribonucleoside triphosphates (dATP, dGTP, dCTP, and dTTP), or analogues of these as discussed above, in a reaction medium comprised of the appropriate salts, metal cations and pH buffering system. Suitable polymerizing agents are enzymes known to catalyze primer- and template-dependent DNA synthesis. The reaction conditions for catalyzing DNA synthesis with these DNA polymerases are well known in the art.

Pyrophosphorolysis is the reverse reaction of DNA polymerasation. In the presence of pyrophosphate, the 3' nucleotide is removed from duplex DNA to generate the triphosphate and the 3' terminal shortened duplex DNA: $[dNMP]_n + PPi \rightarrow [dNMP]_{n-1} + dNTP$. In a method of the present invention where pyrophosphorolysis is required to activate an enriching primer with a blocked 3' end, the extension conditions may comprise an appropriate condition suitable for pyrophosphorolysis, which is well known in the art.

When an enriching primer is extended, an upstream amplification primer or an upstream enriching primer for another diagnostic region is also extended but will stop when their extension strands reach the downstream enriching primer extension product. If the enriching primer comprises a non-copiable (blocking) moiety or the part of the enriching primer on the enriching primer extension product is degraded, a further amplification of the enriching primer extension product is prevented. Herein the expression "further amplification" means specifically an exponential amplification. In some embodiments, a linear (or polynomial amplification) replication of the enriching primer extension product, although not the whole product, is allowed (FIGS. 1, 2, 3 and 4). In another embodiment, both linear and exponential replication of the enriching primer extension product is prevented (FIG. 5). When an annealed enriching primer cannot be extended, it will be dissociated from the template, allowing an exponential amplification of the target sequence flanked by two amplification primers, thereby enriching the desired target sequence.

The method of the present invention further comprises detecting the enriched desired sequence. Detection may be carried out simultaneously with the process of enrichment, for example real-time detection. A detection probe may be included in an enrichment/amplification reaction. Any detection probe can be used; a preferred detection probe is the bridge-probe. Alternative detection may be carried out at the end of the enrichment reaction. A probe may be added at the beginning or end of said enrichment reaction. A melting curve analysis may be performed to detect the suspected variant nucleotide present in the enriched amplification product. It is preferred that a quantitative data is obtained by detection.

It is also possible that detection or verification of the enrichment of the desired nucleic acid is carried out after enrichment, which may be accomplished by a variety of methods, such as a real-time PCR or DNA sequencing.

A typical method of the present invention using a bridge-probe for detection is described in FIG. 7. The bridge-probe not only has an improved ability to distinguish single nucleotide differences due to the short length and high Tm of the first binding portion, but also avoids annealing to the whole length of the enriching primer due to the fact that the second binding portion hybridises to an area outside of the target region, to which the enriching primer is designed to hybridising. It should be appreciated that the bridge-probe in the present invention has wide applications. It can be used to detect a target nucleic acid in conjunction with any amplification method such as PCR, SDA, LCR, RCA, LAMP, NASBA or the like. It can also be used in end-point detection and melting curve analysis.

In one embodiment of the present invention, a method for analyzing a target DNA sequence of a biological sample, said method comprising the steps of
(a) adding to the biological sample an effective amount of amplification primers and a nucleic acid probe, wherein one of said amplification primers and the probe are each labelled with one member of a fluorophore and a quencher such that upon hybridization of the probes with the amplified products the fluorophore and quencher are in a contact quenching relationship, wherein the labelled probe hybridizes to an amplified copy of the target nucleic acid sequence within 5 nucleotides of the labelled primer or the labelled probe hybridizes to the target nucleic acid sequence and a part of the labelled primer;
(b) amplifying the target nucleic acid sequence by an amplification method;
(c) illuminating the biological sample with light of a selected wavelength that is absorbed by said fluorophore; and
(d) detecting the fluorescence emission of the said fluorophore or monitoring temperature dependent fluorescence from said fluorophore. It is preferred that the nucleic acid probe is a bridge-probe.

In another embodiment of the present invention, a method for analyzing a target DNA sequence of a biological sample, said method comprising the steps of
(a) adding to the biological sample an effective amount of amplification primers and two nucleic acid probes that hybridize to adjacent regions of the target sequence, one of said probes being labelled with a fluorophore and the other probe labelled with a quencher of a contact quenching pair such that upon hybridization of the probes with the amplified products the fluorophore and quencher are in a contact quenching relationship, wherein the fluorophore and quencher are within 5 nucleotides of one another;
(b) amplifying the target nucleic acid sequence by an amplification method;
(c) illuminating the biological sample with light of a selected wavelength that is absorbed by said fluorophore; and
(d) detecting the fluorescence emission of the said fluorophore or monitoring temperature dependent fluorescence from said fluorophore. It is preferred that one of the nucleic acid probes is a bridge-probe.

The amplification method can be an isothermal amplification. It is preferred that amplification is thermally cycling amplification, which is preferably a PCR.

The method may further comprise the step of determining a melting profile of the probe and target duplex.

A bridge-probe can be used to genotype SNPs or detect mutations. In one embodiment (FIG. 10A), the first allele-specific primer is labelled with a first fluorophore, for example Fam, while the second allele-specific primer is labelled with second fluorophore, for example Hex. The fluorophore may be attached to a T residue near the 3' end. If the target SNP or mutation is present in a sample, one or both of the allele-specific primers are extended to produce the primer extension strand. A bridge-probe labelled with a quencher at the 3' end, for example BHQ-1, hybridises to the primer extension strand with the first binding portion, while the second binding portion hybridises to the primer sequence. This hybridisation brings the fluorophore and quencher in a close contact quenching relationship. It is very important that the bridging portion of the bridge-probe has 1-3 nucleotides that do not hybridise to the primer so that the primer cannot anneal and extend on the probe. It is also important that the second binding portion that hybridises to the primer is short in length but sufficient to hybridise to the target. The bridging portion can also comprise non-nucleotide chemical moieties so that it cannot act as template and is therefore non-copiable by a polymerase. The hybridisation of the probe to the primer extension product reduces the fluorescence, so the detection of the decrease of a particular fluorescence is an indicative of the presence of the particular SNP or mutation.

In another embodiment (FIG. 10B), one of the amplification primers capable of annealing to a region close to a SNP is labelled with a fluorophore, for example Fam. The fluorophore may be attached to a T residue near the 3' end of the primer. In the detection reaction, the labelled primer is extended to produce the primer extension strand. A bridge-probe labelled with a quencher at the 3' end, for example BHQ-1, hybridises to the primer extension strand with the first binding portion, while the second binding portion hybridises to the primer sequence. The first region that binds to the first binding portion of the bridge-probe contains the SNP or mutation site. This hybridisation makes the fluorophore and quencher in a close contact quenching relationship. It is very important that the bridging portion of the bridge-probe has 1-3 nucleotides that do not hybridise to the primer so that the primer cannot anneal and extend on the probe. It is also important that the second binding portion that hybridises to the primer is short but sufficient to hybridise to the target. The bridging portion can also comprise non-nucleotide chemical moieties so that it cannot act as a template and is therefore non-copiable by a polymerase. The hybridisation of the probe to the primer extension product reduces the label's fluorescence due to quenching effect from the quencher on the probe, so measuring the loss of a particular fluorescence signal at a particular Tm value is indicative of the presence of the particular SNP or mutation. The Tm of the bridge-probe binding can be determined by melting curve analysis.

The methods of the present invention may comprise the step of determining the temperature for maximum rate loss of fluorescence from the probe. The fluorescence of the reaction as a function of temperature may be determined during the polymerase chain reaction.

It would greatly increase the sensitivity of above reactions if single stranded products can be generated by the labelled primer. One method of generating single stranded end products can be the method called Polymerase Chain Displacement Reaction (PCDR) (Fu, G. 2007, International Patent Application No PCT/GB2007/003793). A linked primer capable of inducing the generation of single-stranded end product is incorporated in a PCDR reaction where a bridge-probe can be used to detect a target sequence.

In the hybridization probe design as described in U.S. Pat. No. 6,174,670, a pair of labelled probes are designed to hybridize close to one another on a target sequence and to interact by FRET, wherein the donor and the acceptor fluorophores should not be in immediate contact with each other, as this will decrease the emission intensity of the fluorophores. Therefore, the target sequence for each probe is normally at least 5 nt apart, to prevent contact quenching and to maximize emission from the acceptor. Whereas in the embodiments of this invention, a pair of labelled probes are designed to hybridize close to one another on a target sequence and to interact by contact quenching, wherein the fluorophore and quencher should be in immediate contact with each other, as this will maximize the quenching effect therefore decrease the emission of the fluorophores. Therefore, the target sequence for each probe is normally at least 5 nt, to achieve contact quenching. There are several advantages of using contact quenching rather than FRET. Firstly, the method of the present invention allows maximum multiplexing, whereas both acceptor and donor fluorophores will occupy a detection channel in FRET-based probes, limiting the number of targets that can be detected. Secondly, contact quenching is more effective, therefore the signal decrease from contact quenching is more profound than from FRET. Thirdly, it is more complex to design FRET probes than to design contact quenching probes. For FRET probes, the two labels must be placed within an appropriate distance for FRET to occur; spectral overlap between the emission spectrum of the fluorophore and the absorption spectrum of the acceptor is an important determinant of the FRET efficiency. Spectral overlap is not a significant determinant of quenching efficiency in contact quenching, and quenching efficiencies remain very high in the absence of the spectral overlap.

In a further embodiment, multiple bridge-probes are provided to enable multiplex detection of target nucleic acids, of variant nucleotides in a single target nucleic acid, or for scanning unknown mutations. Each bridge-probe comprises at least two binding portions linked by a bridging portion, wherein the first binding portion is capable of hybridising to a region of interest on a target nucleic acid, and wherein the second binding portion is capable of hybridising to a region adjacent or substantially adjacent to the region of interest on the target nucleic acid. The region of interest on a target nucleic acid can be a diagnostic region with suspected variant nucleotides.

Reagents employed in the methods of the invention can be packaged into assay kits. Assay kits include enriching primers for each diagnostic region of a target nucleic acid sequence, a terminal nucleotide at the 3' end of an enriching primer being either complementary to a suspected variant nucleotide or to the corresponding normal nucleotide, such that, when in use, an extension product of the enriching primer is synthesized when said terminal nucleotide of the enriching primer anneals to the diagnostic region with the corresponding normal nucleotide, whereas the enriching primer is not extendable when said terminal nucleotide of the enriching anneals to the diagnostic region containing the variant nucleotide; and corresponding first and second primers for amplifying a target sequence containing the diagnostic region to which the enriching primer anneals. The kit may also contain other suitably packaged reagents and materials needed for amplification, for example amplification primers, buffers, dNTPs and/or polymerizing means, and detection analysis, as well as instructions for conducting the assay.

In another embodiment, an assay kit includes probes and primers for each diagnostic region of a target nucleic acid sequence, wherein the probes and primers comprise labels which are contact quenching pairs and upon hybridisation to target nucleic acid the labels are in a contact quenching relationship. The kit may also include a bridge-probe which comprises at least two binding portions linked by a bridging portion, wherein the first binding portion is capable of hybridising to a first region of a template nucleic acid, and wherein the second binding portion is capable of hybridising to a second region adjacent or substantially adjacent to the first region of the template nucleic acid. The first region of the template nucleic acid may be a region of interest on a target nucleic acid, which can be a diagnostic region with suspected variant nucleotides.

Thus certain kits of the invention are those adapted for performance of the methods defined herein—for example including combinations of enriching and amplification primers and written instructions for performing any of the methods defined herein. Thus in respect of the first aspect, typically the enriching primer will have a 3' terminal nucleotide which is either complementary to the suspected variant nucleotide, or to the corresponding normal nucleotide. Typically the amplification primer be adapted to anneal to a target such that the 3' end of the amplification primer is adjacent to or upstream of the 5' end of the enriching primer. The enriching primer preferably comprises a moiety that renders the extension product of the enriching primer unsuitable for an exponential amplification i.e. makes it non-copiable as described above. Optionally the enriching primer also comprises modified nucleotides or linkages which render the whole or part of the enriching primer resistant to nuclease cleavage. The kit may also include a nucleic acid polymerase comprises a 5' exonuclease activity.

The invention will now be further described with reference to the following non-limiting examples. Other embodiments of the invention will occur to those skilled in the art in light of these.

The disclosure of all references cited herein, inasmuch as it may be used by those skilled in the art to carry out the invention, is hereby specifically incorporated herein by cross-reference.

EXAMPLES

Example 1

All primers and probes used in the subsequent experiments were synthesized by EUROGENTEC, UK. Real-time PCR and melting curve analysis were performed on Bio-Rad Chromo4 real-time PCR or Stratagene MX3005P machine. Primers were designed to amplify a target DNA sequence BRAF gene from plasmids comprising a normal BRAF gene fragment and a mutated BRAF gene fragment (harbouring V599E). The sequence of this gene fragment comprises the sequence:

ggaaagcatctcacctcatcctaacacatttcaagccccaaaaatcttaa
aagcaggttatataggctaaatagaactaatcattgttttagacatactt
attgactctaagaggaaagatgaagtactatgttttaaagaatattatat
tacagaattatagaaattagatctcttacctaaactcttcataatgcttg
ctctgataggaaaatgagatctactgttttcctttacttactacacctca
gatatatttcttcatgaagacctcacagtaaaaataggtgattttggtct
agctacagtgaaatctcgatggagtgggtcccatcagtttgaacagttgt
ctggatccattttgtggatggtaagaattgaggctattttccactgatt
aaattttggccctgagatgctgctgagttactagaaagtcattgaaggt
ctcaactatagtattttcatagttcccagtattcac The sequences of primers are:

```
BrafF2      GGAAAGCATCTCACCTCATCCTAACAC
BrafEndR2   GACTTTCTAGTAACTCAGCAGCATCTCA
BraFAMR2    GGACCCACTCCATCG1GATTTC2A
```

Wherein "1" is dR-biotin, "2" is Phosphorothioate linkage. All nucleic acid sequences are written 5' to 3' unless otherwise stated. Herein BraFAMR2 is an enriching primer.

Primers were diluted to a final concentration of 10 μM. Amplification was performed using the following ingredients and conditions: 10×PCR Buffer (stoffel fragment buffer from Applied Biosystems) 2.5 μl, 10 mM dNTPs 0.5 μl, each primer, if added, 0.5 μl, Stoffel fragment, AmpliTaq DNA polymerase (5 U/μl) 0.25 μl, plasmid DNA 0.5 μl ($10^5$ molecules) and water to final volume of 25 μl. Reactions were carried out at 94° C. for 1 min; 40 cycles of 15 sec at 94° C., 30 sec at 57° C., 1 sec at 68° C., 15 sec at 60° C. on BioMetra PCR machine. The primers added in reactions are as follows:

|  | Tube number | | | | | | | | |
|---|---|---|---|---|---|---|---|---|---|
|  | 1 | 2 | 3 | 4 | 5 | 6 | 7 | 8 | 9 |
| BrafF2 | + | + | + | + | + | + | + | + | + |
| BrafEndR2 | + | + | − | + | + | − | + | + | − |
| BrafFamR2 | − | + | + | − | + | + | − | + | + |
| Normal DNA | − | − | − | − | − | − | + | + | + |
| Mutated DNA | + | + | + | − | − | − | − | − | − |
| M/N = 1/100DNA | − | − | − | + | + | + | − | − | − |

M/N=1/100DNA means the plasmid DNA containing mutated DNA and normal DNA at the ratio of 1:100.

After PCR the amplified DNA products were loaded in an agarose gel. DNA from tube number 2, 4, 5, 7, and 8 were sequenced using primers BrafendR2 and BrafendinR2 (having a sequence GCCTCAATTCTTACCATCCACAA (SEQ ID NO: 5)) by GATC ltd. The mutation enriched PCR product from PCR tube 5 showed that the sequenced base is mutated type, whereas non-enriched PCR product from tube 4 showed that the sequence base is normal type.

Example 2

Melting Curve Analysis of a Bridge-Probe Hybridised to Matched and Mismatched Templates A bridge-probe PadLfam is designed having a sequence GAGCCGTCGGTGGTCaaaaaaaaaaCAT-GACGAGCCCTA (SEQ ID NO: 6), wherein the 5' end is labelled with 6-Fam, and the 3' end is labelled with BHQ1. The Binding portions are in uppercase letters, the bridging portion is in lowercase letters.

Two template oligos are also designed which are: PadLTemp ATAGACCACCGACGGCTCATT-AGGGCTCGTCATGTAAC (SEQ ID NO: 7), and PadLTempM ATAGACCACCGACGGCTCATT-AGGGCTAGTCATGTAAC (SEQ ID NO: 8), wherein PadLTempM contains a single nucleotide difference which is underlined.

The bridge-probe PadLfam hybridises to its templates in a form like FIG. 6A. A melting curve analysis was performed as shown in FIG. 9A. A 6 degree Tm difference is observed between matched template (line 2) and template with a single nucleotide difference (line 1) hybridised to the bridge-probe.

Example 3

Different Length of the Bridging Portions of a Bridge Probe Affects Tm

Two bridge-probes SunDab and SunDabA13 are designed as follows, wherein the 3' ends are labelled with Dabcyl. The probe SunDab has no bridging portion, whereas probe SunDabA13 contains a bridging portion with 13 As. A second probe SunFam contains two regions complementary to the first binding portion and second binding portion of the bridge-probe and is labelled with 6-Fam at 5' end. Another oligonucleotide SunTemp is designed to have a region complementary to a part of the second probe. Alignments showing the binding regions are as follows, wherein "F" means 6-Fam, "Q" means dabcyl, "-" means no nucleotide, "I" means complementary bases, "P" indicates phosphate group.

```
SunFam     5' FCACCGCGCTTAGTTACATGACGAGCCGTGTAGCGTGGACGACAGAGG-P 3'
              IIIIII                    IIIIIIIIIIIIIIIIIIII
Sundab     3' QGTGGCG-------------------CACATCGCACCTGCTGTCTCC 5'

SunFam     5' FCACCGCGCTTAGTTACATGACGAGCCGTGTAGCGTGGACGACAGAGG-P 3'
              IIIIII                    IIIIIIIIIIIIIIIIIIII
SunDabA13  3' QGTGGCG----AAAAAAAAAAAAA---CACATCGCACCTGCTGTCTCC 5'

SunFam     5' FCACCGCGCTTAGTTACATGACGAGCCGTGTAGCGTGGACGACAGAGG-P 3'
                    IIIIIIIIIIIIIIIIIIIIIIIIIIIII
SunTemp    3' CCCAAAGTGGCGCGAATCAATGTACTGCTCGGGATTACTC 5'
```

Melting curve analysis was performed with the following oligos combination:

|  | Tube number | | | | | |
|---|---|---|---|---|---|---|
|  | 1 | 2 | 3 | 4 | 5 | 6 |
| SunFam | + | + | + | + | + | + |
| SunDab | − | + | − | + | − | − |
| SunTemp | − | − | + | + | − | + |
| SunDabA13 | − | − | − | − | + | + |

The result is shown in FIG. 9B, which demonstrates that the bridging-portion difference (tube 2 and 5) has a big impact on the Tm. The bridge-probe SunDabA13 having a long bridging portion shows a high Tm especially for the binding portion with the short sequence (tube 5).

Example 4

Amplification Using Labels of Contact Quenching Pair

Amplification primers and probes are BrafEndinR2, GCCTCAATTCTTACCATCCACAA; (SEQ ID NO: 5) BrafEndR2, GACTTTCTAGTAACTCAGCAGCATCTCA (SEQ ID NO: 3); BraFAMR2, GGACCCACTCCATCG1GATTTC2A ("1" is dR-biotin, "2" is Phosphorothioate linkage; (SEQ ID NO: 4); BraPCDRF, ctacacctcagatatatttcttcatgaag (SEQ ID NO: 13), labelled with 5' Fam; BraBridge, ATCACCTATTTTTACT-GTGAGGTCaaagaGGTGTAG (SEQ ID NO: 14), labelled with 3' BHQ-1.

The amplification primer BraPCDF and the probe BraBridge are each labelled with Fam and BHQ-1 respectively such that upon hybridization of the probes with the amplified products the fluorophore and quencher are in contact quenching relationship.

Primers were diluted to a final concentration of 10 μM. Amplification was performed using the following ingredients and conditions: 10×PCR Buffer (NEB thermo buffer) 2.5 μl, 10 mM dNTPs 0.5 μl, each primer, if added, 0.5 μl, Vent (exo-) or Taq DNA polymerase (5 U/μl) 0.25 μl, plasmid DNA 0.5 μl (10⁵ molecules) and water to final volume of 25 μl. Reactions were carried out at 94° C. for 1 min; 36 cycles of 9 sec at 94° C., 30 sec at 51° C. (read fluorescence), 30 sec at 72° C., 30 sec at 51° C. (read fluorescence), and 30 sec at 72° C. on BioRad chromo4 real-time PCR machine. The primers added in reactions are as follows:

| | Tube number | | | | | | | |
|---|---|---|---|---|---|---|---|---|
| | 1 | 2 | 3 | 4 | 5 | 6 | 7 | 8 |
| BraPCDRF | + | + | + | + | + | + | + | + |
| BraBRIDGE | + | + | + | + | + | + | + | + |
| BraFamR2 | − | + | − | + | − | + | − | + |
| BrafEndinR2 | + | + | − | − | + | + | − | − |
| BrafendR2 | − | − | + | + | − | − | + | + |
| Vent | + | + | + | + | − | − | − | − |
| Taq | − | − | − | − | + | + | + | + |
| Normal DNA(#3744) | + | + | + | + | + | + | + | + |

Amplifying the target nucleic acid sequence by real-time PCR method; illuminating the biological sample with light of a 492 nm wavelength that is absorbed by Fam; and detecting the fluorescence emission of the said fluorophore and monitoring temperature dependent fluorescence from said fluorophore.

Degreased fluorescent signals were observed in all reactions, indicating the targets are present in all samples.

Example 5

Amplification primer pairs are designed such that one primer contains a 5' tail sequence which is identical to the other primer in the pair.

Amplification primers and probe are: JKR3 ccF2, GATGCTCTGAGAAAGGCATTAGAAAG-CATCTTTATTATGGCAGAGAGAA (SEQ ID NO: 15); JKR3, GATGCTCTGAGAAAGGCATTAGA (SEQ ID NO: 16); JKFamdR, GTTTTACTTACTCTCGTCTCCAC6GAA (SEQ ID NO: 17), in this primer "T" at position 11 is BHQ-1(dT), "6" is Fam-dR.

Primers are diluted to a final concentration of 10 μM. Amplification is performed using the following ingredients and conditions: 10×PCR Buffer (NEB thermo buffer) 3 μl, 5 μl betain, 10 mM dNTPs 0.5 μl, primer JKR31.25 μl, primer JKR3 ccF2 0.5 μl, JKFamdR 1 μl, if added, Taq DNA polymerase (5 U/μl) 0.25 μl, plasmid DNA 0.5 μl (10⁵ molecules) and water to final volume of 25 μl. Reactions are carried out at 94° C. for 1 min; 40 cycles of 15 sec at 95° C., 18 sec at 61° C., 18 sec at 54° C., 18 sec at 72° C., 20 sec at 60° C., 25 sec at 72° C., and 30 sec at 72° C. (data is collected at each temperature) on Stratagene MX3005 real-time PCR machine. The plasmid template is a mixture of mutated DNA containing V617F and wild type DNA. The method comprises amplifying the target nucleic acid sequence by real-time PCR; illuminating the biological sample with light of a 492 nm wavelength that is absorbed by Fam; and detecting the fluorescence emission of the said fluorophore and monitoring temperature dependent fluorescence from said fluorophore.

The denatured JKR3 ccF2 primer extension product forms a stem-loop structure under annealing condition. The R3 primer is unable to anneal due to the stem-loop structure. The enriching primer JKFamdR anneals to the loop portion and is extended if it anneals to the mutated nucleotide. The extension of JKFamdR primer opens up the stem-loop structure, thereby allowing the R3 primer to anneal and extension. The extension of R3 primer degrades the enriching primer extension product due to the 5' to 3' exonuclease nature of Taq polymerase. The enriching primer extension product also can be displaced if the polymerase has a strand displacement activity. If the enriching primer anneals to the wild type DNA, which contains a nucleotide forming a mismatch with the terminal nucleotide of the primer, the enriching primer is not extended, whereby the stem-loop structure is intact. This results in enriching the DNA containing the mutated nucleotide. The enriching primer comprises labels Fam and BHQ. The degradation of enriching primer extension product gives fluorescence signal. This reaction allows enrichment and detection of the target nucleic acid in the single tube.

The invention claimed is:

1. A method for enriching and optionally detecting a target nucleic acid with at least one variant nucleotide from a nucleic acid population in a sample, said method comprising:
   (a) treating the sample with an enriching primer and an amplification primer for a first strand of the target nucleic acid sequence to create a mixture of duplexes wherein the mixture of duplexes comprises the enriching primer and the amplification primer annealed to the target nucleic acid under hybridising conditions, wherein the nucleotide sequence of said enriching primer is such that it is substantially complementary to a diagnostic region where the variant nucleotide is located but wherein a nucleotide at, or within 1, 2, or 3 nucleotides of the 3' terminus is complementary to the corresponding normal nucleotide, and wherein the amplification primer is annealed to the target nucleic acid such that the 3' end of the amplification primer is upstream of the 5' end of the enriching primer;
   (b) maintaining the mixture of step (a) under extension conditions, which comprise nucleoside triphosphates and a nucleic acid polymerase which does not have strand displacement activity, to extend the annealed primers, if extendable, to synthesize primer extension products;
   (c) repeating steps (a) and (b) in an amplification reaction which is PCR; and
   (d) optionally detecting the enriched target nucleic acid, wherein extension of the enriching primer occurs when it is annealed to the diagnostic region of the target nucleic acid having the normal nucleotide to synthesize an enriching primer extension product, wherein the enriching primer extension product is not fully digested or displaced by the nucleic acid polymerase, whereby the enriching primer extension product thereby blocks the extension initiated from the amplification primer when the amplification primer is annealed to the target nucleic acid having the normal nucleotide, wherein the annealed enriching primer is not extendable when it anneals to the diagnostic region containing the variant nucleotide, whereby the enriching primer is dissociated from the target sequence under the extension conditions, thereby allowing extension of the amplification primer to pass through the diagnostic region containing the variant nucleotide leading to exponential amplification of the target nucleic acid containing the variant nucleotide, and wherein the enriching primer comprises a moiety that renders the extension product of the enriching primer unsuitable for an exponential amplification, thereby permitting preferential exponential amplification of the target nucleic acid having the variant nucleotide.

2. The method according to claim 1, wherein the 3' terminal nucleotide of the enriching primer is complementary to the corresponding normal nucleotide.

3. The method according to claim 1, wherein said moiety is a blocking moiety which is not suitable as a template for nucleic acid polymerase, wherein the replication of all or part of said enriching primer is blocked.

4. The method according to claim 3, wherein said blocking moiety is a hydrocarbon arm, non-nucleotide linkage, peptide nucleic acid, nucleotide derivatives, abasic ribose, or dye.

5. The method according to claim 3, wherein said blocking moiety is located less than 3, 6, or 18 nucleotides away from the 3' terminus of the enriching primer.

6. The method according to claim 1, wherein said moiety is a tail sequence of nucleotides or non-nucleic acid 5' to the priming portion of the enriching primer, wherein the 5' tail sequence is complementary or substantially complementary to a binding site in the enriching primer extension product for a further amplification primer, which further amplification primer is required for replication of the enriching primer extension product.

7. The method according to claim 1, wherein said enriching primer comprises modified nucleotides or linkages which render the whole or part of the enriching primer resistant to nuclease cleavage.

8. The method according to claim 7, wherein the last nucleotide or last 5 nucleotides or linkages at the 3 end and/or 5' end are modified such that the enriching primer is resistant to nuclease cleavage.

9. The method according to claim 1, wherein said nucleoside triphosphates comprise at lease one modified deoxynucleoside triphosphate, which renders a part or whole of an extended strand resistant to a nuclease cleavage, wherein said enriching primer comprises natural nucleotides and phosphodiester linkages, which render a part or whole of the enriching primer degradable by a nuclease activity.

10. The method according to claim 1, wherein in step (a) the reaction mixture comprises a further enriching primer and/or an amplification primer for the second strand of the target sequence which is complementary to said first strand of target sequence.

11. The method according to claim 1, wherein said nucleic acid polymerase is a thermostable enzyme.

12. The method according to claim 1 further comprising detecting the enriched target nucleic acid.

13. The method according to claim 1, farther comprising detecting the enriched target nucleic acid, wherein said detection is mediated by a bridge probe,
   which bridge probe comprises at least two binding portions linked by a bridging portion, wherein the first binding portion is capable of hybridising to a first region of the target nucleic acid,
   and wherein the second binding portion is capable of hybridising to a second region of the target nucleic acid that is adjacent or substantially adjacent to the first region of the target nucleic acid,
   and wherein the first region of the target nucleic acid contains the variant nucleotide,
   wherein said bridging portion comprises a sequence with at least one nucleotide or at least one non-nucleotide chemical moiety which is incapable of hybridising to the target nucleic acid.

14. The method according to claim 13, wherein the first binding portion of the bridge probe hybridises to the target nucleic acid with matched or mismatched nucleotides at different melting temperatures, which are measured and are indicative of the presence or absence of the variant nucleotide.

15. The method according to claim 13, wherein either
   (i) one end of said bridging portion is attached to the 5 end of the first binding portion and another end of said bridging portion is attached to the 3' end of the second binding portion, or
   (ii) one end of said bridging portion is attached to the 5' end of the first binding portion, and another end of said bridging portion is attached to the 5' end of the second binding portion, or wherein one end of said bridging portion is attached to the 3' end of the first binding portion, and another end of said bridging portion is attached to the 3' end of the second binding portion.

16. The method according to claim 13, wherein:
 (i) the ends of said bridge probe face towards each other when the bridge probe hybridises to a target nucleic acid, or
 (ii) the ends of said bridge probe face in opposite directions when the bridge probe hybridises to a target nucleic acid.

17. The method according to claim 13, wherein the bridge probe and/or one or more of the primers comprise detection labels.

18. The method according to claim 17, wherein the first binding portion is attached to a first label and the second binding portion is attached to a second label, and either
 (i) said first label and second label are contact quenching pairs, wherein one of the labels is a quencher,
 and wherein upon hybridization of the bridge probe with the target sequence, the first and second labels are in a contact quenching relationship, or
 (ii) said first label and second label are fluorescence energy transfer pair,
 and wherein upon hybridization of the bridge probe with the target sequence, the first and second labels are in a fluorescence resonance energy transfer (FRET) relationship.

19. The method according to claim 13, wherein the second binding portion and a part of the amplification primer, which is capable of hybridising with the second binding portion of the bridge probe, are each attached to one member of a fluorophore and a quencher binding pair,
 such that upon hybridization of the bridge probe with the primer extension strand, the fluorophore and quencher are in a contact quenching relationship.

20. The method according to claim 18 or 19, wherein said quencher is selected from the group consisting of a non-fluorescent entity, a nanoparticle, and a G residue or multiple G residues.

21. The method according to claim 13, wherein the ends of said bridge probe face in the same direction when the bridge probe hybridises to a target nucleic acid.

* * * * *

SEQUENCE LISTING

<160> NUMBER OF SEQ ID NOS: 17

<210> SEQ ID NO 1
<211> LENGTH: 486
<212> TYPE: DNA
<213> ORGANISM: Artificial sequence
<220> FEATURE:
<223> OTHER INFORMATION: BRAF gene fragment

<400> SEQUENCE: 1
ggaaagcatc tcacctcatc ctaacacatt tcaagcccca aaaatcttaa aagcaggtta      60
tataggctaa atagaactaa tcattgtttt agacatactt attgactcta agaggaaaga     120
tgaagtacta tgttttaaag aatattatat tacagaatta tagaaattag atctcttacc     180
taaactcttc ataatgcttg ctctgatagg aaaatgagat ctactgtttt cctttactta     240
ctacacctca gatatatttc ttcatgaaga cctcacagta aaaataggtg attttggtct     300
agctacagtg aaatctcgat ggagtgggtc ccatcagttt gaacagttgt ctggatccat     360

```
tttgtggatg gtaagaattg aggctatttt tccactgatt aaattttttgg ccctgagatg    420 ctgctgagtt actagaaagt cattgaaggt ctcaactata gtattttcat agttcccagt    480
attcac                                                                486
```

<210> SEQ ID NO 2
<211> LENGTH: 27
<212> TYPE: DNA
<213> ORGANISM: Artificial sequence
<220> FEATURE:
<223> OTHER INFORMATION: Primer BrafF2

<400> SEQUENCE: 2

```
ggaaagcatc tcacctcatc ctaacac                                          27
```

<210> SEQ ID NO 3
<211> LENGTH: 28
<212> TYPE: DNA
<213> ORGANISM: Artificial sequence
<220> FEATURE:
<223> OTHER INFORMATION: Primer BrafEndR2

<400> SEQUENCE: 3

```
gactttctag taactcagca gcatctca                                         28
```

<210> SEQ ID NO 4
<211> LENGTH: 23
<212> TYPE: DNA
<213> ORGANISM: Artificial sequence
<220> FEATURE:
<223> OTHER INFORMATION: Enriching primer BraFAMR2
<220> FEATURE:
<221> NAME/KEY: misc_feature
<222> LOCATION: (16)..(16)
<223> OTHER INFORMATION: n is dR-biotin
<220> FEATURE:
<221> NAME/KEY: misc_feature
<222> LOCATION: (22)..(23)
<223> OTHER INFORMATION: phosphorothioate linkage

<400> SEQUENCE: 4

```
ggacccactc catcgngatt tca                                              23
```

<210> SEQ ID NO 5
<211> LENGTH: 23
<212> TYPE: DNA
<213> ORGANISM: Artificial sequence
<220> FEATURE:
<223> OTHER INFORMATION: Primer BrafendinR2

<400> SEQUENCE: 5

```
gcctcaattc ttaccatcca caa                                              23
```

<210> SEQ ID NO 6
<211> LENGTH: 39
<212> TYPE: DNA
<213> ORGANISM: Artificial sequence
<220> FEATURE:
<223> OTHER INFORMATION: Bridge-probe PadLfam

<400> SEQUENCE: 6

```
gagccgtcgg tggtcaaaaa aaaaacatga cgagccta                              39
```

<210> SEQ ID NO 7
<211> LENGTH: 38
<212> TYPE: DNA
<213> ORGANISM: Artificial sequence

```
<220> FEATURE:
<223> OTHER INFORMATION: Template oligo PadLTemp

<400> SEQUENCE: 7
atagaccacc gacggctcat tagggctcgt catgtaac                    38

<210> SEQ ID NO 8
<211> LENGTH: 38
<212> TYPE: DNA
<213> ORGANISM: Artificial sequence
<220> FEATURE:
<223> OTHER INFORMATION: Template oligo PadLTempM

<400> SEQUENCE: 8
atagaccacc gacggctcat tagggctagt catgtaac                    38

<210> SEQ ID NO 9
<211> LENGTH: 47
<212> TYPE: DNA
<213> ORGANISM: Artificial sequence
<220> FEATURE:
<223> OTHER INFORMATION: Probe SunFam
<220> FEATURE:
<221> NAME/KEY: misc_feature
<222> LOCATION: (1)..(1)
<223> OTHER INFORMATION: 6-Fam attachment

<400> SEQUENCE: 9
caccgcgctt agttacatga cgagccgtgt agcgtggacg acagagg           47

<210> SEQ ID NO 10
<211> LENGTH: 27
<212> TYPE: DNA
<213> ORGANISM: Artificial sequence
<220> FEATURE:
<223> OTHER INFORMATION: Bridge-probe SunDab
<220> FEATURE:
<221> NAME/KEY: misc_feature
<222> LOCATION: (27)..(27)
<223> OTHER INFORMATION: Dabcyl attachment

<400> SEQUENCE: 10
cctctgtcgt ccacgctaca cgcggtg                                27

<210> SEQ ID NO 11
<211> LENGTH: 40
<212> TYPE: DNA
<213> ORGANISM: Artificial sequence
<220> FEATURE:
<223> OTHER INFORMATION: Bridge-probe SunDabA13
<220> FEATURE:
<221> NAME/KEY: misc_feature
<222> LOCATION: (40)..(40)
<223> OTHER INFORMATION: Dabcyl attachment

<400> SEQUENCE: 11
cctctgtcgt ccacgctaca caaaaaaaaa aaaagcggtg                  40

<210> SEQ ID NO 12
<211> LENGTH: 40
<212> TYPE: DNA
<213> ORGANISM: Artificial sequence
<220> FEATURE:
<223> OTHER INFORMATION: Oligonucleotide SunTemp

<400> SEQUENCE: 12
ctcattaggg ctcgtcatgt aactaagcgc ggtgaaaccc                  40
```

<210> SEQ ID NO 13
<211> LENGTH: 29
<212> TYPE: DNA
<213> ORGANISM: Artificial sequence
<220> FEATURE:
<223> OTHER INFORMATION: Amplification primer BraPCDF

<400> SEQUENCE: 13
ctacacctca gatatatttc ttcatgaag                              29

<210> SEQ ID NO 14
<211> LENGTH: 36
<212> TYPE: DNA
<213> ORGANISM: Artificial sequence
<220> FEATURE:
<223> OTHER INFORMATION: Probe BraBridge

<400> SEQUENCE: 14
atcacctatt tttactgtga ggtcaaagag gtgtag                      36

<210> SEQ ID NO 15
<211> LENGTH: 49
<212> TYPE: DNA
<213> ORGANISM: Artificial sequence
<220> FEATURE:
<223> OTHER INFORMATION: Primer JKR3ccF2

<400> SEQUENCE: 15
gatgctctga gaaaggcatt agaaagcatc tttattatgg cagagagaa        49

<210> SEQ ID NO 16
<211> LENGTH: 23
<212> TYPE: DNA
<213> ORGANISM: Artificial sequence
<220> FEATURE:
<223> OTHER INFORMATION: Primer JKR3

<400> SEQUENCE: 16
gatgctctga gaaaggcatt aga                                    23

<210> SEQ ID NO 17
<211> LENGTH: 27
<212> TYPE: DNA
<213> ORGANISM: Artificial sequence
<220> FEATURE:
<223> OTHER INFORMATION: Primer JKFamdR
<220> FEATURE:
<221> NAME/KEY: misc_feature
<222> LOCATION: (12)..(12)
<223> OTHER INFORMATION: n is BHQ-1 (dT)
<220> FEATURE:
<221> NAME/KEY: misc_feature
<222> LOCATION: (24)..(24)
<223> OTHER INFORMATION: n is Fam-dR

<400> SEQUENCE: 17
gttttactta cnctcgtctc cacngaa                                27